US010016207B2

United States Patent
Suzuki et al.

(10) Patent No.: US 10,016,207 B2
(45) Date of Patent: Jul. 10, 2018

(54) MEDICAL MANIPULATOR

(71) Applicant: Karl Storz SE & Co. KG, Tuttlingen (DE)

(72) Inventors: Tsuneyoshi Suzuki, Kanuma (JP); Hirofumi Mugishima, Utsunomiya (JP)

(73) Assignee: Karl Storz SE & Co. KG, Tuttlingen (DE)

( * ) Notice: Subject to any disclaimer, the term of this patent is extended or adjusted under 35 U.S.C. 154(b) by 401 days.

(21) Appl. No.: 14/511,691

(22) Filed: Oct. 10, 2014

(65) Prior Publication Data

US 2015/0025571 A1    Jan. 22, 2015

Related U.S. Application Data

(63) Continuation of application No. PCT/JP2013/060946, filed on Apr. 11, 2013.

(30) Foreign Application Priority Data

Apr. 12, 2012  (JP) ................. 2012-090794

(51) Int. Cl.
*A61B 17/29*    (2006.01)
*A61B 34/00*    (2016.01)
(Continued)

(52) U.S. Cl.
CPC .......... *A61B 17/29* (2013.01); *A61B 17/2909* (2013.01); *A61B 34/70* (2016.02); *A61B 18/1445* (2013.01); *A61B 2017/003* (2013.01); *A61B 2017/00314* (2013.01); *A61B 2017/00398* (2013.01); *A61B 2017/00477* (2013.01); *A61B 2017/2927* (2013.01);
(Continued)

(58) Field of Classification Search
CPC . A61B 17/29; A61B 17/2902; A61B 18/1445; A61B 2017/2908; A61B 2017/2901; A61B 2017/2927; A61B 2017/2929; A61B 2017/2939; A61B 2017/2947; A61M 25/0133; A61M 25/0147
USPC ................................. 606/205, 206
See application file for complete search history.

(56) References Cited

U.S. PATENT DOCUMENTS

| 5,766,196 A | 6/1998 | Griffiths |
| 5,797,536 A * | 8/1998 | Smith ............... A61B 17/0682 |
| | | 227/175.1 |

(Continued)

FOREIGN PATENT DOCUMENTS

JP    4391762 B2    12/2009

*Primary Examiner* — Christopher L Templeton
*Assistant Examiner* — Majid Jamialahmadi
(74) *Attorney, Agent, or Firm* — Whitmyer IP Group LLC

(57) ABSTRACT

This medical manipulator is provided with a distal-end moving section including an end effector. The distal-end moving section includes a rotating sleeve (a distal-end rotator) which is able to rotate integrally with the end effector about a roll axis and has a hollow cylindrical portion, and a distal-end fulcrum block (rotary support cylinder) which is provided so as to be able to change orientation in relation to the axial direction of a shaft and rotatably supports the rotating sleeve at an inner peripheral section. A part of an opening/closing driving transmission section (actuating means) for transmitting an opening/closing driving force to the end effector is disposed inside of the distal-end moving section.

9 Claims, 12 Drawing Sheets

(51) Int. Cl.
*A61B 34/30* (2016.01)
*A61B 18/14* (2006.01)
*A61B 17/00* (2006.01)

(52) U.S. Cl.
CPC ............ *A61B 2017/2929* (2013.01); *A61B 2017/2936* (2013.01); *A61B 2017/2939* (2013.01); *A61B 2017/2946* (2013.01); *A61B 2017/2947* (2013.01); *A61B 2034/306* (2016.02)

(56) References Cited

U.S. PATENT DOCUMENTS

| | | |
|---|---|---|
| 2004/0225323 A1 | 11/2004 | Nagase et al. |
| 2008/0147113 A1* | 6/2008 | Nobis .................... A61B 17/29 606/205 |
| 2010/0076483 A1 | 3/2010 | Imuta |
| 2010/0249497 A1 | 9/2010 | Peine et al. |

* cited by examiner

MEDICAL MANIPULATOR

FIELD OF THE INVENTION

The present invention relates to a medical manipulator that is used when a surgical operation, and in particular an endoscopic surgical operation, is carried out, and in which a distal end working unit thereof having an end effector can be subjected to a rolling operation within an unlimited range of rotation.

BACKGROUND OF THE INVENTION

In an endoscopic surgical operation (also referred to as "laparoscopic surgery"), a plurality of holes are punctured in the abdomen and such of a patient, trocars (cylindrical instruments) are inserted through the holes, and a laparoscope (camera) and a plurality of forceps are inserted into the body cavity via each of the trocars. Grippers, scissors, and blades of an electric scalpel or the like for gripping biological tissue are mounted to the tip of the forceps as an end effector.

If the laparoscope and the forceps are inserted into the body cavity, an operator operates the forceps while viewing a state of the inner portion of the abdominal cavity, which is shown on a monitor that is connected to the laparoscope. Since the surgical procedure does not require a laparotomy, the burden on the patient is decreased, which reduces the number of days for postoperative recovery and leaving the hospital. For this reason, the fields that such an operative method can be applied to are expected to expand.

Other than typical forceps that are not provided with joints at distal end portions thereof, as forceps that are inserted through a trocar, forceps referred to as a medical manipulator have been developed that are provided with joints at distal end portions and which can carry out a rolling operation or a tilting operation of an end effector (for example, refer to Japanese Patent No. 4391762). In accordance with such a medical manipulator, a high degree of operational freedom is facilitated in the body cavity, manual procedures are made easy, and thus there are a large number of medical cases to which the medical manipulator may be applied.

SUMMARY OF THE INVENTION

Incidentally, in the medical manipulator, it is desirable for the distal end working unit including the end effector to have a high degree of freedom and to have a movable range that is as wide as possible. For example, if the range of rotation of the rolling operation of the distal end working unit were unlimited, such a feature could be expected to contribute to the smooth performance of procedures such as ligation or the like. On the other hand, as the degree of freedom of the distal end working unit is increased, it is easy for the structure of the medical manipulator to become complex.

The present invention has been devised while taking into consideration the aforementioned problems, and has the object of providing a medical manipulator, which is equipped with a distal end working unit having a high degree of freedom, without increasing the complexity of the structure of the medical manipulator.

To realize the above object, the medical manipulator according to the present invention comprises a handle, a shaft that extends from the handle, a distal end working unit having an end effector, and which is connected while capable of being tilted with respect to the shaft, and further which is capable of undergoing a rolling operation, and an operating means disposed between the handle and the distal end working unit and which actuates the end effector. The distal end working unit includes a distal end side rotating body, which is capable of being rotated integrally with the end effector about a roll axis and further has a hollow cylindrical portion, and a rotating support cylinder, which is capable of being changed in posture with respect to an axial direction of the shaft, and rotatably supports the distal end side rotating body on an inner circumferential portion thereof. Further, a portion of the operating means is disposed inside the distal end working unit.

According to the structure of the present invention as described above, since the operating means (e.g., a drive member for opening and closing or rotating the end effector, wires for supplying electricity to the end effector, etc.) can be arranged substantially in the center of the distal end working unit by having the distal end side rotating body be of a hollow shape, a structure can be adopted in which the range of rotation of the rolling operation of the distal end working unit is unlimited. Further, since the rotating support cylinder is arranged not on the inside of the distal end side rotating body but on the outer side thereof, the hollow portion of the distal end side rotating body can suitably ensure an arrangement space for the operating means, together with enabling the structure of the distal end working unit to be simplified. Accordingly, a medical manipulator is provided, which is equipped with the distal end working unit having a high degree of freedom, without increasing the complexity of the structure of the medical manipulator.

In the above-described medical manipulator, the rotating support cylinder is capable of rotating centrally about a tilt axis that intersects with the shaft axis on the distal end of the shaft. In addition, a pair of joint pins, which are disposed on the tilt axis, may be provided at a joint between the shaft and the distal end working unit, and another portion of the operating means may be inserted through a gap provided between the pair of joint pins.

According to the above structure, the arrangement space for the operating means can easily be assured in the interior of the joint.

In the above-described medical manipulator, the rotating support cylinder may be made up from a plurality of segments, which rotatably support the distal end side rotating body inside thereof, as a result of being connected together in a circumferential direction.

According to the above structure, the plural segments are connected in the circumferential direction, thereby constituting the rotating support cylinder that supports the distal end side rotating body on an inner circumferential portion thereof. Consequently, during assembly of the distal end working unit, by mutually joining the plurality of segments by welding or the like so as to surround the distal end side rotating body with the plural segments, a configuration can easily be constructed in which the rotating body is arranged inside of the segments, and a rotary support member is provided on the outer side of the rotating body.

According to the present invention, a medical manipulator is provided, which is equipped with the distal end working unit having a high degree of freedom, without increasing the complexity of the structure of the medical manipulator.

DETAILED DESCRIPTION OF THE INVENTION

Hereinafter, preferred embodiments of a medical manipulator according to the present invention will be described in detail below with reference to the accompanying drawings.

First Embodiment

Figure 1:
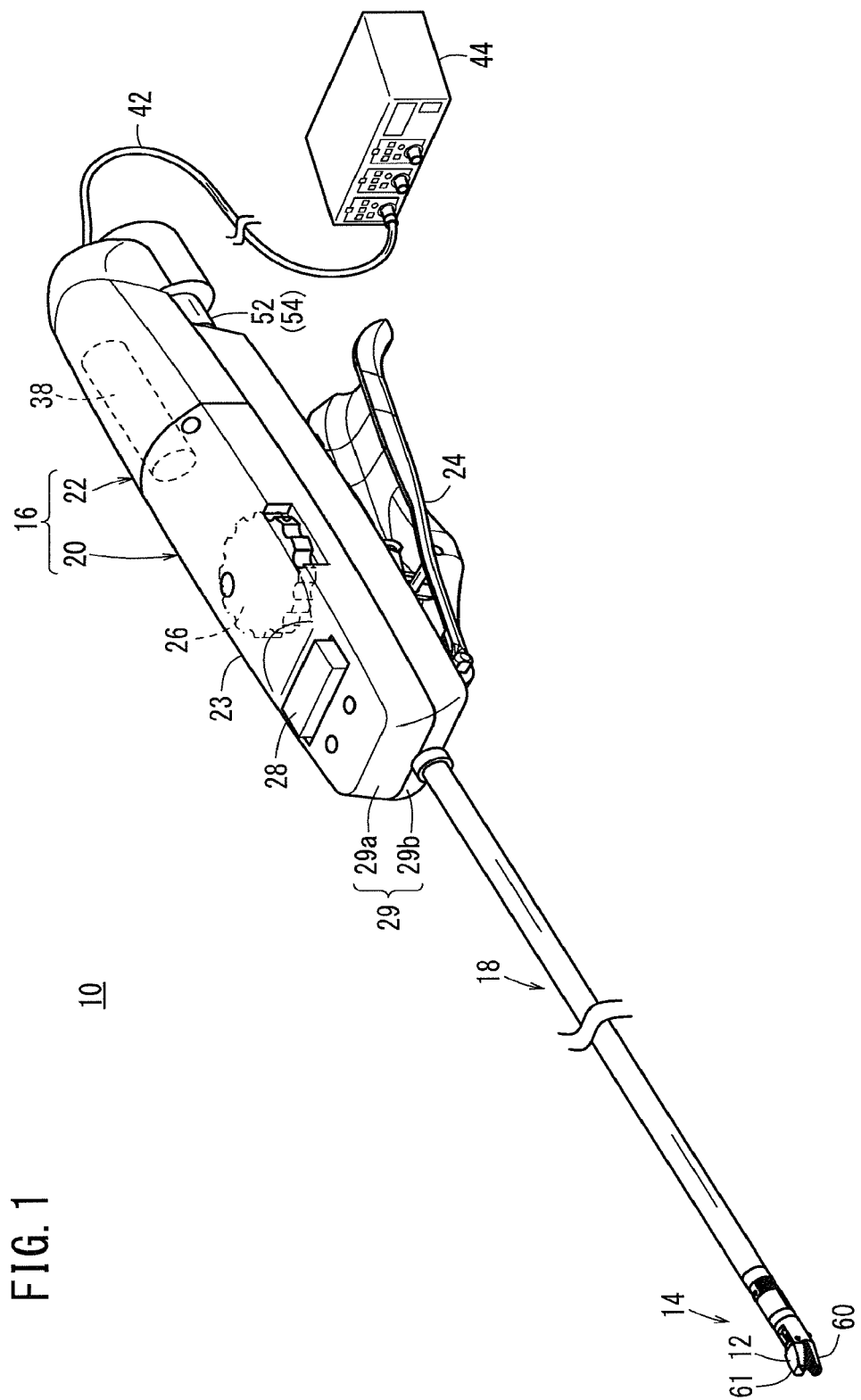
FIG. 1 is a perspective view with partial omission of a medical manipulator according to a first embodiment of the present invention.

FIG. 1 is a partially-omitted, perspective view of a medical manipulator 10 according to a first embodiment of the present invention. The medical manipulator 10 is a medical implement that grasps a needle, a suture or a part of the living body or touches the living body using the end effector 12 provided at a distal end thereof, and carries out a predetermined treatment. Corresponding to the type of end effector 12 provided at the distal end, the medical manipulator 10 can be configured to have a grasping forceps, a needle driver, a monopolar electric scalpel, a bipolar electric scalpel, or the like.

Below, initially, the structure of a medical manipulator 10 in which a needle driver is used as one embodiment will be described in outline, followed by a detailed description of the structure of respective parts thereof.

The medical manipulator 10 is equipped with a distal end working unit 14 including an end effector 12, a handle 16 that drives the end effector 12, and a shaft 18 that interconnects the end effector 12 and the handle 16. The end effector 12 is a portion that carries out a surgical treatment, and in the illustrated example, the end effector 12 includes first and second gripper members 60, 61, and is configured to have a gripper mechanism that carries out an opening and closing operation on the basis of a predetermined opening and closing operation shaft. The end effector 12 is not limited to a gripper mechanism, and may be configured to have scissors or an electrode for an electric scalpel.

The posture of the distal end working unit 14 including the end effector 12 can be changed at a plurality of degrees of freedom with respect to the shaft 18. In the present embodiment, the distal end working unit 14 can carry out a "tilting operation" (swinging operation) in which the distal end working unit 14 is operated to tilt in left and right directions with respect to an axis of the shaft 18, and a "rolling operation" in which the distal end working unit 14 is rotated about the axis of the shaft 18 in the longitudinal direction of the distal end working unit 14. Instead of swinging in left and right directions, the tilting operation may be an operation in which the distal end working unit 14 is operated in a tilting manner in upward and downward directions with respect to the axis of the shaft 18.

The shaft 18 is an oblong and small diameter tubular member. A plurality of members configured to make up a power transmission mechanism are inserted into or are arranged in a hollow portion of the shaft 18. Such a power transmission mechanism transmits, from the handle 16 to the distal end working unit 14, power that is necessary for carrying out the opening and closing operation of the end effector 12, and the rolling operation and the tilting operation of the distal end working unit 14.

The handle 16 includes a handle main body 20 including a plurality of operating units, and a drive unit 22 including a motor 38 that is capable of being attached to and detached from the handle main body 20. When the motor 38 is driven in a state in which the drive unit 22 is mounted on the handle main body 20, a driving force from the motor 38 is transmitted to the distal end working unit 14. Thus, the form of use of the medical manipulator 10 can be one in which, concerning a manipulator main body thereof, which includes the handle main body 20, the shaft 18, and the distal end working unit 14, the manipulator main body can be discarded after being used a predetermined number of times, whereas the drive unit 22 can be used repeatedly many times by changing the manipulator main body that is connected to the drive unit 22.

The handle main body 20 comprises a body portion 23 that is connected to a proximal end of the shaft 18, a lever 24 (opening and closing operating unit) provided on the body portion 23, a tilt wheel 26 (tilt operating unit) provided on the body portion 23, and a rolling switch 28 (rolling operating unit) provided on the body portion 23.

The body portion 23 makes up a part that is gripped by a user when the medical manipulator 10 is used. In the present embodiment, the body portion 23 is constituted in the form of a stick that extends over a certain length in the axial direction of the shaft 18. The body portion 23 includes a casing 29 made up from an upper cover 29a and a lower cover 29b, with drive components such as pulleys, gears, wires, etc., being arranged in the interior of the casing 29.

A lever 24 for performing an opening and closing operation of the end effector 12 is disposed on a lower part of the body portion 23, and is swingably mounted upward and downward about the distal end side thereof which serves as a support point. According to the present embodiment, the lever 24 is constructed as a manual manipulating part, in which an opening and closing operation of the end effector 12 is carried out by mechanically transmitting to the end effector 12 of the distal end working unit 14 an operating force applied with respect to the lever 24. More specifically, a structure is provided in which the end effector 12 is opened when the lever 24 is opened, and the end effector 12 is closed when the lever 24 is closed.

The tilt wheel 26 for carrying out a tilting operation of the distal end working unit 14 is disposed near the center in the longitudinal direction of the body portion 23. The tilt wheel 26 is constituted as a manual manipulating part, having a portion in the circumferential direction thereof that is exposed from the casing 29. When the tilt wheel 26 is operated by being rotated, the operating force applied thereto is transmitted mechanically to the distal end working unit 14 through a tilting operation power transmission system, which is disposed internally in the handle 16 and the shaft 18, whereupon the distal end working unit 14 is tilted in a non-parallel direction (in left and right directions or upward and downward directions) with respect to the axis of the shaft 18.

The rolling switch 28 for carrying out a rolling operation of the distal end working unit 14 is disposed on an upper portion in the vicinity of the front end of the body portion 23. In the present embodiment, the rolling switch 28 is constituted as an electrical manipulating part, which supplies an operating command to the motor 38 through a controller 44.

When the rolling switch 28 is pressed, a signal corresponding to the pressed position is transmitted to the controller 44 through a connector 54 and a cable 42, and under the control of the controller 44, the motor 38 is driven and a driving force from the motor 38 is transmitted to the distal end working unit 14, whereby the distal end working unit 14 is rotated about the longitudinal axis of the distal end working unit 14. In the present embodiment, the distal end working unit 14 is rotated clockwise when a right-hand part of the rolling switch 28 is pressed, and the distal end working unit 14 is rotated counterclockwise when a left-hand part of the rolling switch 28 is pressed.

Figure 2:
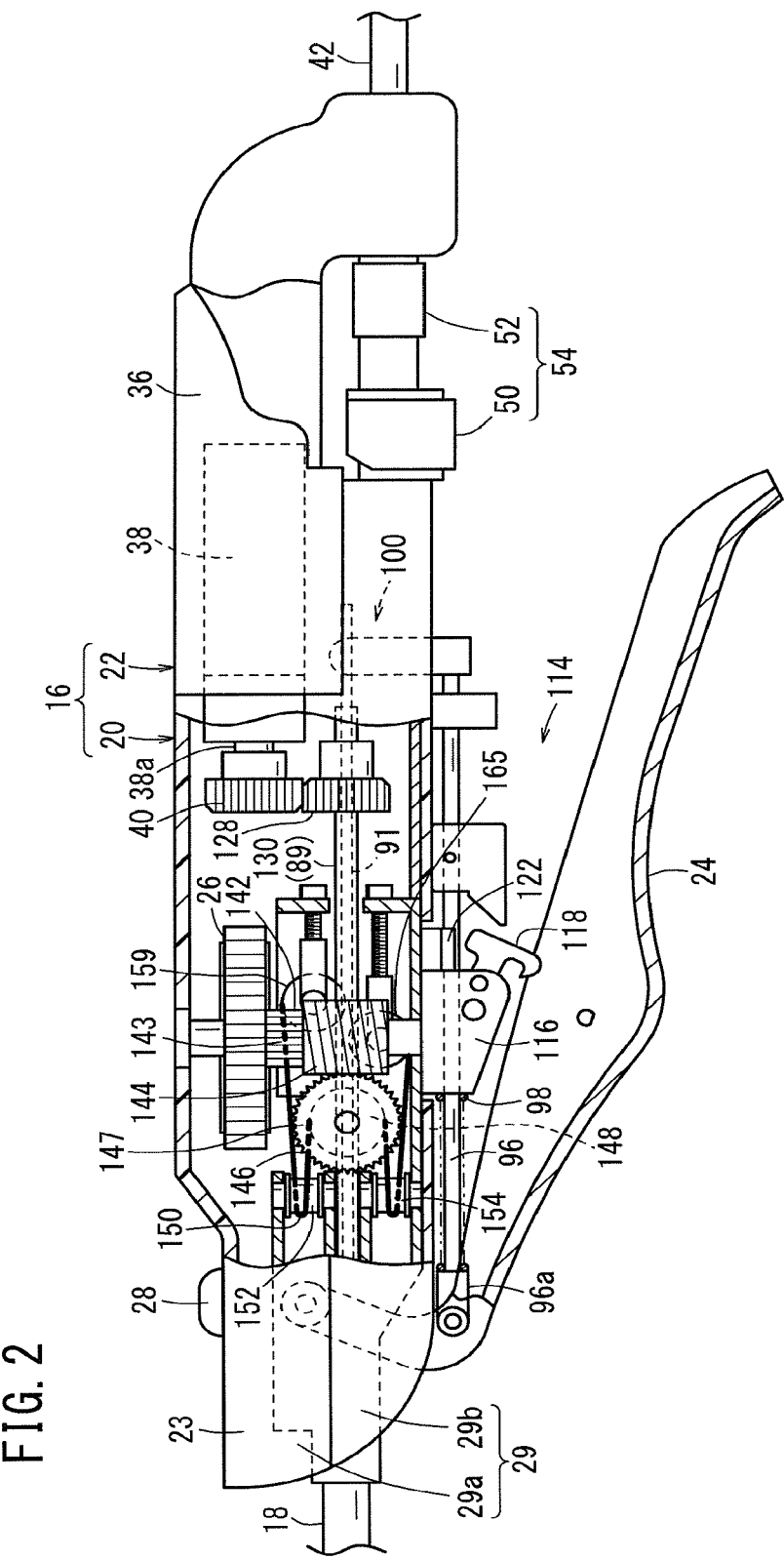
FIG. 2 is a side view partially shown in cross section of the medical manipulator illustrated in FIG. 1.

As shown in FIG. 2, the drive unit 22 includes a housing 36, a motor 38 (drive source) disposed inside the housing 36, and a drive gear 40 (pinion gear) which is fixed to an output shaft of the motor 38. The drive unit 22 is detachable from the rear of the handle main body 20. In a condition in which the drive unit 22 is attached (connected) to the handle main body 20, the housing 36 forms a portion that makes up the casing 29 of the handle 16 together with the handle main body 20. In the present embodiment, the housing 36 extends over a certain length in the longitudinal direction of the handle main body 20. The drive gear 40, which is fixed to the output shaft of the motor 38, projects toward the distal end side more than the distal end of the housing 36.

The drive unit 22 is connected to the controller 44 through a cable 42 that includes a power line and a signal line. The controller 44 controls the supply of power and driving of the motor 38, and receives electrical power from an external power source. When the rolling switch 28 is operated, a signal corresponding to the operation thereof is transmitted to the controller 44, and the controller 44 controls driving of the motor 38. Some or all of the functions of the controller 44 may be incorporated integrally in the drive unit 22.

Upon attachment of the drive unit 22 to the body portion 23 of the handle main body 20, the drive gear 40, which is fixed to the output shaft 38a of the motor 38, is brought into meshing engagement with a driven gear 128 that is disposed inside the body portion 23. In this condition, when the motor 38 is rotated, the rotary driving force of the motor 38 is transmitted to the side of the handle main body 20 through the drive gear 40 and the driven gear 128.

As shown in FIG. 2, a handle side connector 50 is disposed on the rear of the body portion 23 of the handle main body 20, and a unit side connector 52 is disposed on the rear of the drive unit 22. In a condition in which the drive unit 22 is attached to the handle main body 20, the handle side connector 50 and the unit side connector 52 are mutually connected electrically to each other. More specifically, the connector 54 is constituted from the handle side connector 50 and the unit side connector 52. If the rolling switch 28 is operated in a condition in which the handle side connector 50 and the unit side connector 52 are connected, a signal corresponding to the state of the rolling switch 28 is transmitted to the controller 44 through the connector 54 and the signal line of the cable 42, and under the control of the controller 44, the motor 38 that is mounted in the drive unit 22 is driven.

Figure 3:
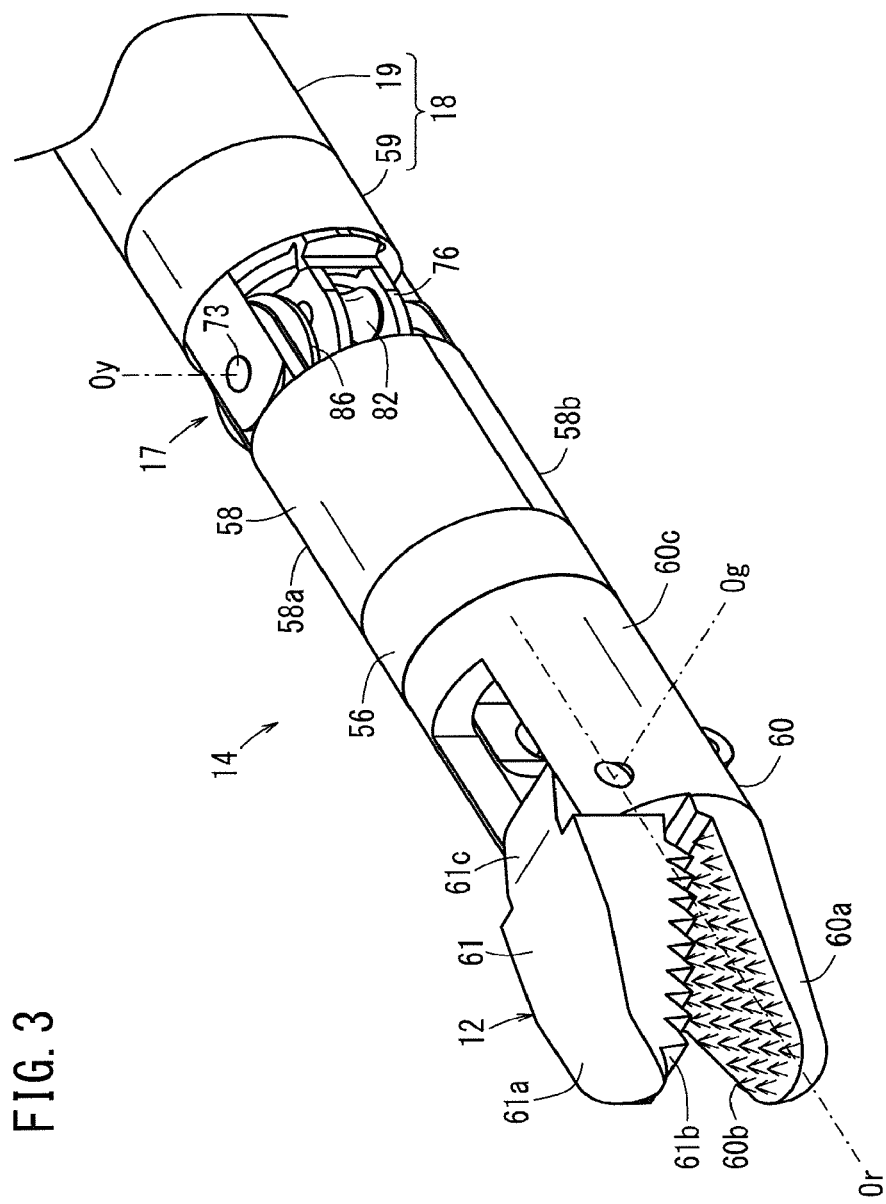
FIG. 3 is a perspective view of a distal end working unit.
Figure 4:
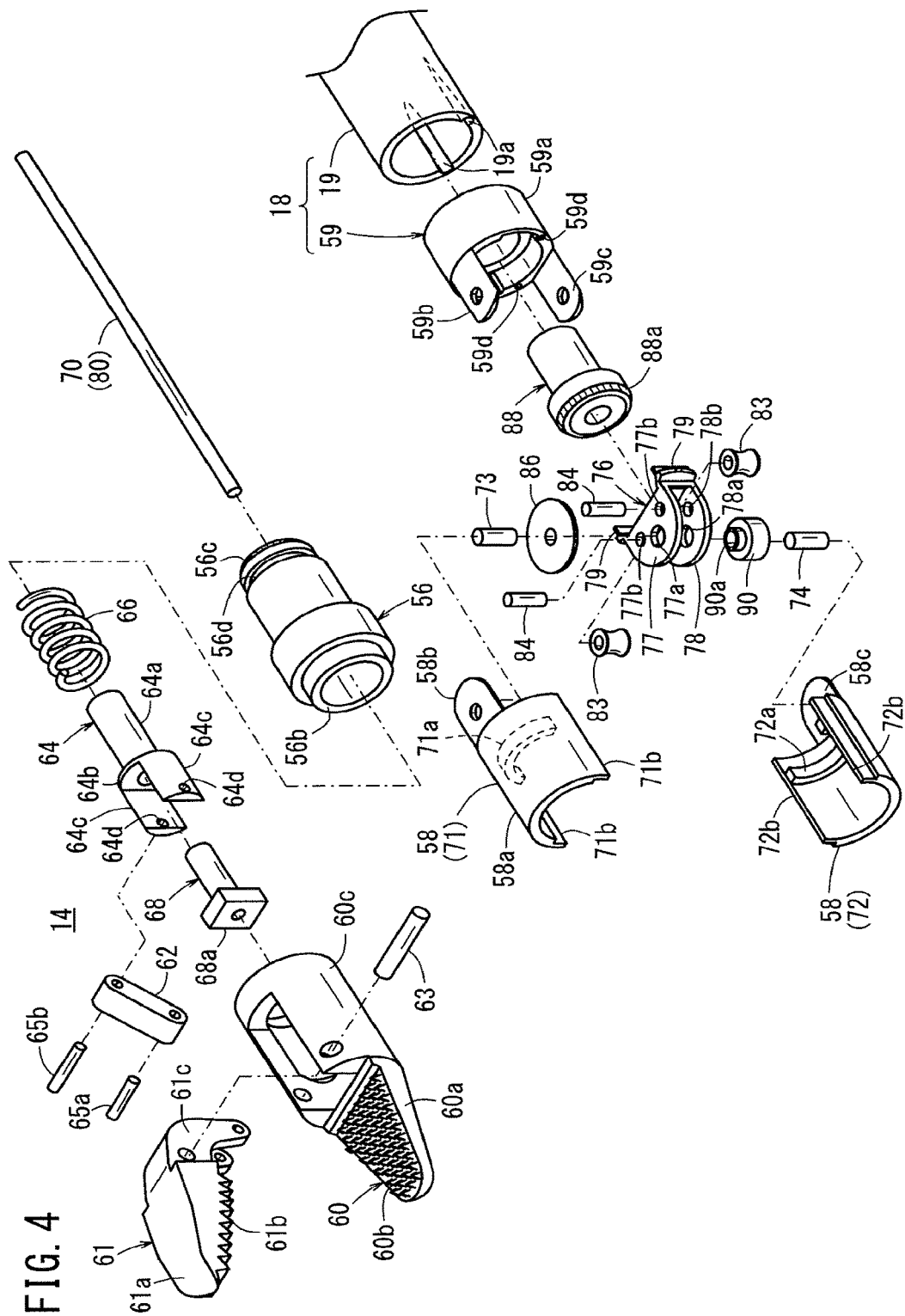
FIG. 4 is an exploded perspective view of the distal end working unit.
Figure 5:
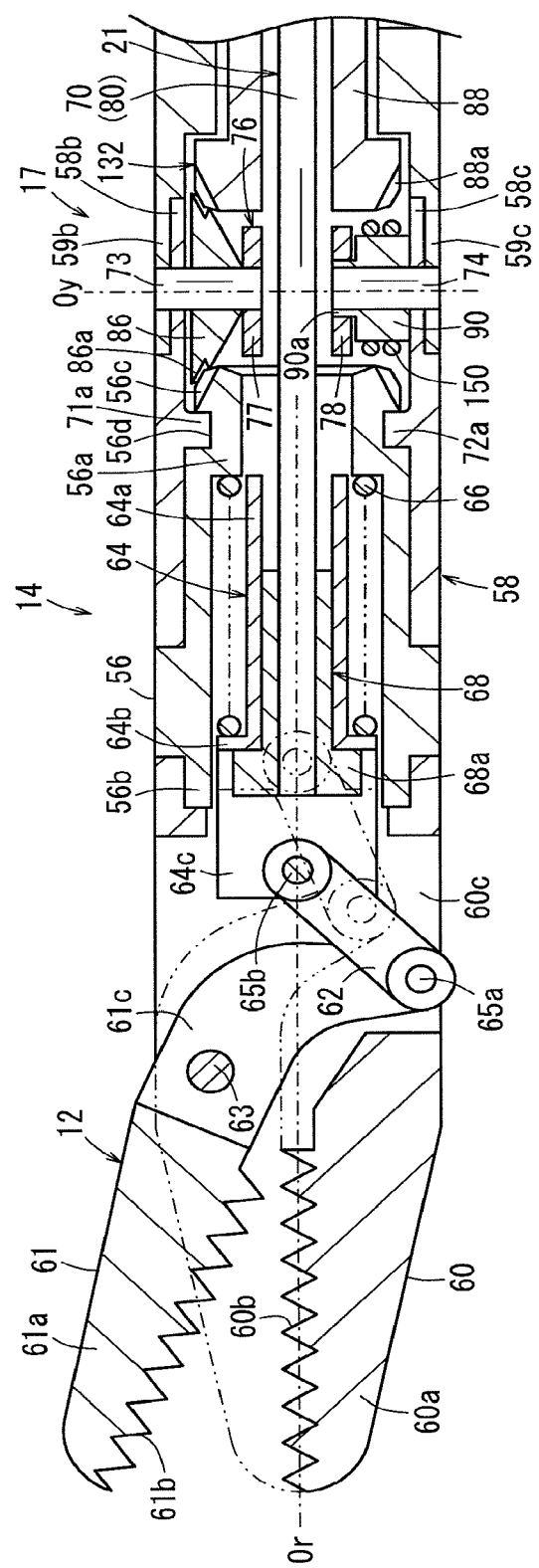
FIG. 5 is a vertical cross-sectional view of the distal end working unit.

FIG. 3 is a perspective view showing the distal end working unit 14 which is connected to the distal end of the shaft 18. FIG. 4 is an exploded perspective view of the distal end working unit 14. FIG. 5 is a vertical cross-sectional view of the distal end working unit 14. As shown in FIGS. 3 through 5, the distal end working unit 14 includes the end effector 12 that is capable of being opened and closed, a rotating sleeve 56 (distal end side rotating body) of a hollow cylindrical shape, which is fixed to the end effector 12, and a distal end side fulcrum block 58 (rotating support cylinder) that rotatably supports the rotating sleeve 56 in an axially rotatable manner on an inner circumferential portion thereof.

The end effector 12 is made up from a first gripper member 60 and a second gripper member 61. The first gripper member 60 and the second gripper member 61 are connected by a pin 63 so as to be capable of rotating about a gripper axis Og. A gripping face 60b, which is formed with a large number of irregularities thereon for providing a non-slip surface, is provided on a jaw portion 60a of the first gripper member 60. Similarly, a gripping face 61b, which is formed with a large number of irregularities thereon for providing a non-slip surface, is provided on a jaw portion 61a of the second gripper member 61. A base portion 60c of the first gripper member 60 is substantially cylindrical in shape, and on the base portion 60c, a base portion 61c of the second gripper member 61 is connected by a pin 63, so as to be capable of rotating with respect thereto. An object to be gripped, for example a needle or the like, is gripped by the gripping face 60b of the first gripper member 60 and the gripping face 61b of the second gripper member 61.

The base portion 61c of the second gripper member 61 is connected through a link member 62 to a transmission member 64. The base portion 61c and the link member 62, as well as the link member 62 and the transmission member 64, are connected rotatably by respective pins 65a, 65b. The transmission member 64 includes a guide tube 64a, a flange 64b disposed on a distal end of the guide tube 64a, and two support arms 64c that extend mutually in parallel in the direction of the distal end from edges of the flange 64b. The transmission member 64 is arranged so as to be movable in the axial direction in the interior of the rotating sleeve 56. The pin 65b is fitted into pin holes 64d that are provided in the support arms 64c.

A compression spring 66 is arranged between the transmission member 64 and the rotating sleeve 56. One end of the compression spring 66 abuts against the flange 64b of the transmission member 64, whereas the other end thereof abuts against a stepped portion 56a provided on an inner circumferential portion of the rotating sleeve 56, so that the transmission member 64 normally is elastically biased in the direction of the distal end.

An end collar 68 is inserted into the transmission member 64 from the distal end side. A distal end of the end collar 68 is constituted as an engaging bulge 68a that comes into abutment and engages with the distal end surface of the guide tube 64a of the transmission member 64. The end collar 68 is fixed to a distal end of a pull wire 70 that passes through a joint 17 (see FIGS. 4 and 6) between the distal end working unit 14 and the shaft 18.

The pull wire 70 forms a member that moves in an advancing and retracting manner in the interior of the shaft 18 and the interior of the distal end working unit 14 responsive to an operation made with respect to the lever 24 of the handle 16. When the pull wire 70 is displaced in the direction of the proximal end, the transmission member 64 is pushed toward the proximal end by the end collar 68 to which the pull wire 70 is fixed, whereby the transmission member 64 is displaced in the direction of the proximal end in opposition to the biasing force of the compression spring 66. Accompanying displacement of the transmission member 64 toward the proximal end, the second gripper member 61, which is connected to the link member 62, is rotated in a closing direction with respect to the first gripper member 60. In FIG. 5, the first gripper member 60 is shown by an imaginary line, in a state of being closed to a position at which the gripping face 61b of the second gripper member 61 and the gripping face 60b of the first gripper member 60 are placed in contact.

From the state of being closed to a position at which the gripping face 61b of the second gripper member 61 and the gripping face 60b of the first gripper member 60 are in contact, when the pull wire 70 and the end collar 68 are advanced, since the transmission member 64 is urged forward by the elastic force of the compression spring 66, the first gripper member 60 rotates through the link member 62 in a direction to open with respect to the second gripper member 61, and is restored to its original state. This operation is referred to as an opening and closing operation of the end effector 12.

In the present embodiment, although for the end effector 12, a case has been described in which the first gripper member 60 is constituted as a fixed member and the second gripper member 61 is constituted as a movable member, both of the gripper members may be constituted as movable members.

At a reduced diameter portion 56b on the distal end thereof, the rotating sleeve 56 is fitted and fixedly attached to the base portion 60c of the first gripper member 60. In the rotating sleeve 56, a bevel gear part 56c is provided on the proximal end thereof, and an annular recess 56d is disposed at a position more toward the distal end side than the bevel gear part 56c. The end effector 12, the rotating sleeve 56, the transmission member 64, the end collar 68, and the compression spring 66 are capable of rotating in unison with respect to the distal end side fulcrum block 58, about the longitudinally directed roll axis Or of the distal end working unit 14.

The distal end side fulcrum block 58 is capable of being changed in posture with respect to the axial direction of the shaft 18, and rotatably supports the rotating sleeve 56 on an inner circumferential portion thereof. The distal end side fulcrum block 58 is made up from a plurality of segments, which rotatably support the rotating sleeve 56 inside thereof, as a result of being connected together in a circumferential direction. More specifically, in the present embodiment, the distal end side fulcrum block 58 is made up from a semicircular upper block 71 (segment), and a semicircular lower block 72 (segment). The upper block 71 and the lower block 72 are assembled together to form a hollow cylindrical shape. The outer diameter of the distal end side fulcrum block 58 preferably is 3 mm to 8 mm, and in the present embodiment, a description is given in which the outer diameter thereof is 5 mm. The inner diameter of the distal end side fulcrum block 58 preferably is 2 mm to 7 mm, and in the present embodiment, a description is given in which the inner diameter thereof is 4 mm.

On both ends in the circumferential direction of the upper block 71, outer diameter side thin-walled portions 71b are provided, in which the outer diameter sides are made thin-walled, by making the inner diameters thereof greater in diameter than other portions of the upper block 71. On both ends in the circumferential direction of the lower block 72, inner diameter side thin-walled portions 72b are provided, in which the inner diameter sides are made thin-walled, by making the outer diameters thereof more reduced in diameter than other portions of the lower block 72. The outer diameter side thin-walled portions 71b and the inner diameter side thin-walled portions 72b are joined together by a suitable joining means, such as by welding or an adhesive or the like, whereby the upper block 71 and the lower block 72 are fixed mutually to one another.

Respective arcuate projections 71a, 72a are provided on inner circumferential portions of the upper block 71 and the lower block 72. By engagement between the arcuate projections 71a, 72a and an annular recess 56d that is provided on the rotating sleeve 56, the rotating sleeve 56 is connected rotatably, and is immovable in the axial direction, with respect to the distal end side fulcrum block 58.

Due to providing the arcuate projections 71a, 72a and the annular recess 56d in this manner, in the event that the distal end side fulcrum block 58 were tentatively made from a single cylindrical component and not constructed in a divided manner, the rotating sleeve 56 could not be arranged in the hollow portion of the distal end side fulcrum block 58. Thus, in the present embodiment, the distal end side fulcrum block 58 is constructed from the upper block 71 and the lower block 72. Therefore, when the distal end working unit 14 is assembled, by surrounding the rotating sleeve 56 with the upper block 71 and the lower block 72, and mutually joining the upper block 71 and the lower block 72 to each other by welding or the like, the rotating sleeve 56 can be assembled in a state of being supported rotatably on the inner circumferential portion of the distal end side fulcrum block 58.

The arcuate projections 71a, 72a have a predetermined amount of projection (e.g., 0.7 mm) toward the longitudinal center axis, and have a predetermined width (e.g., 1 mm) in the longitudinal direction in order to obtain a sufficient strength. Further, in the present embodiment, although one each of the arcuate projection 71a on the inner circumferential portion of the semicircular upper block 71, and the arcuate projection 72a on the inner circumferential portion of the semicircular lower block 72 are provided, the invention is not limited to this feature, and the arcuate projection 71a may be constituted from a plurality of projections. For example, the arcuate projections 71a may be arranged at intervals of 30° on the inner circumferential portion of the upper block 71. In this case, the arcuate projection 71a would be constituted from three arcuate projections.

The distal end side fulcrum block 58 and a shaft side fulcrum block 59 are connected together rotatably about the tilt axis Oy by joint pins 73, 74. The shaft side fulcrum block 59 is fixed to the distal end of the hollow shaft main body 19 that constitutes the body portion of the shaft 18. The shaft 18 is constituted from the shaft side fulcrum block 59 and the shaft main body 19.

In the present embodiment, the tilt axis Oy is set in the vertical direction. However, the tilt axis Oy may be set in a different direction that intersects the axis of the shaft main body 19. The distal end side fulcrum block 58 includes a cylindrical portion 58a, and tongues 58b, 58c, which project mutually in parallel toward the proximal side from upper and lower portions on the proximal end of the cylindrical portion. The shaft side fulcrum block 59 includes a cylindrical portion 59a, and tongues 59b, 59c, which project mutually in parallel toward the distal end side from upper and lower portions on the distal end of the cylindrical portion 59a. Joint pins 73, 74 are fitted into the tongues 58b, 58c of the distal end side fulcrum block 58, and into the tongues 59b, 59c of the shaft side fulcrum block 59.

Figure 6:
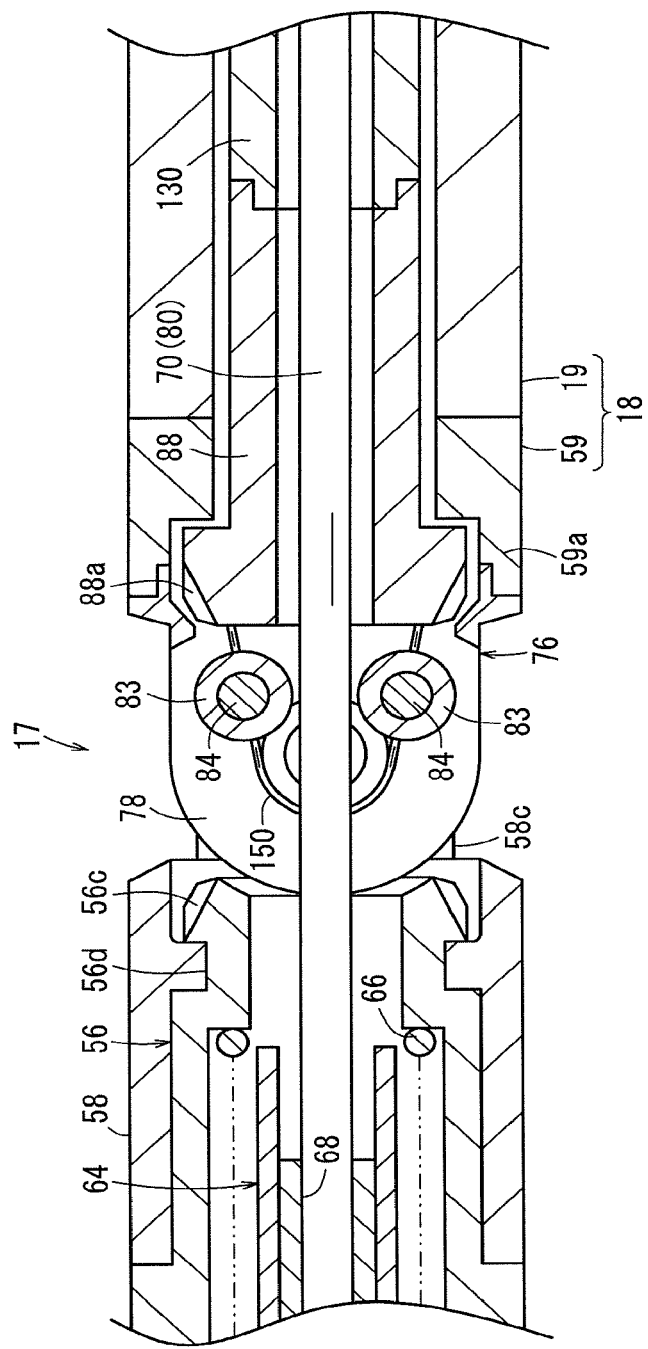
FIG. 6 is a vertical cross-sectional view of a joint and an area in the vicinity thereof, showing a state in which the distal end working unit is arranged in a straight manner with respect to a shaft.

As shown in FIGS. 4 through 6, a support block 76 is mounted on the distal end of the cylindrical portion 59a of the shaft side fulcrum block 59. The support block 76 includes upper and lower support plates 77, 78 that confront one another mutually in parallel, and connectors 79 that are connected to both left and right rear end portions of the support plates 77, 78. A pin hole 77a, into which the upper side joint pin 73 is inserted, and left and right pin holes 77b, into which upper ends of two pins 84 are inserted respectively, are provided in the upper side support plate 77. A hole 78a, into which a reduced diameter upper end portion 90a of the driven pulley 90 is inserted, and left and right pin holes 78b, into which lower ends of the two pins 84 are inserted respectively, are provided in the lower side support plate 78.

In the vicinity of the tilt axis Oy with respect to the shaft 18 of the distal end working unit 14, guide rollers 83 that serve to guide the pull wire 70 are disposed on both left and right sides of the pull wire 70 and the distal end working unit 14. Because the guide rollers 83 are disposed in this manner, when the distal end working unit 14 is bent with respect to the shaft 18, the pull wire 70 is supported by the guide rollers 83, whereby the bent portion of the pull wire 70 is supported in the vicinity of the tilting fulcrum of the distal end working unit 14. Therefore, when the distal end working unit 14 is bent (inclined) with respect to the shaft 18, within the distal end working unit 14, advancing of the distal end of the pull wire 70 can be prevented or suppressed. Thus, the gripped condition of the target object by the end effector 12 can suitably be maintained.

The guide rollers 83 are supported rotatably at an interval in the left and right direction by two pins 84, which are arranged mutually in parallel. The above-mentioned pull wire 70 extends between the two guide rollers 83. By such a structure, even if an opening and closing drive transmission member 80 is subjected to advancing and retracting movements under a condition in which the distal end working unit 14 is bent with respect to the shaft 18, since the guide rollers 83 are rotated accompanying advancing and retracting movements of the pull wire 70, the pull wire 70 can be advanced and retracted smoothly.

As shown in FIG. 5, the joint 17 that is present between the distal end working unit 14 and the shaft 18 includes the two joint pins 73, 74, which are arranged on the tilt axis Oy. In addition, the pull wire 70, which constitutes part of the opening and closing drive transmission member 80, is capable of advancing and retracting in a direction intersecting the axial direction of the joint pins 73, 74, through a gap that is provided between the pair of joint pins 73, 74. According to this structure, an arrangement space for the pull wire 70 can easily be assured in the interior of the joint 17.

Between the upper side support plate 77 and the tongue 58b, a bevel gear 86 (intermediate member) is supported rotatably by the joint pin 73. The bevel gear 86 is rotatable independently of the support plate 77 and the tongue 58b. The teeth 86a of the bevel gear 86 are enmeshed with the bevel gear part 56c provided on the base end of the rotating sleeve 56, and a bevel gear part 88a that is provided on the distal end of a gear member 88. The gear member 88 on which the bevel gear part 88a is provided is a hollow cylindrical member, with the pull wire 70 being inserted internally through the hollow portion thereof.

Upon rotation of the gear member 88, the rotational force of the gear member 88 is transmitted to the rotating sleeve 56 through the bevel gear 86 and the bevel gear part 56c, and the rotating sleeve 56 together with the end effector 12 that is fixed thereto are rotated about the roll axis Or with respect to the distal end side fulcrum block 58. This operation is referred to as a rolling operation of the distal end working unit 14.

Between the lower side support plate 78 and the tongue 58c, the driven pulley 90 is supported rotatably by the joint pin 74. The driven pulley 90 is fixed to an inner surface of the tongue 58c of the distal end side fulcrum block 58. Accordingly, the driven pulley 90 and the distal end side fulcrum block 58 including the tongue 58c are capable of swinging in unison with respect to the shaft side fulcrum block 59. A tilting operation wire 150 is trained around the driven pulley 90. A portion of the wire 150 is fixed to the driven pulley 90, and the wire 150 passes through the interior of the shaft 18 up to the side of the handle 16. The structural arrangement of the wire 150 will be described in detail later.

When the driven pulley 90 is driven and rotated by the wire 150, the distal end side fulcrum block 58, which is fixed to the driven pulley 90, is rotated integrally with the driven pulley 90. As a result, the distal end working unit 14 including the distal end side fulcrum block 58, the rotating sleeve 56 and the end effector 12 is rotated about the tilt axis Oy with respect to the shaft 18. This operation is referred to as a tilting operation of the distal end working unit 14.

Assuming a condition in which the distal end working unit 14 is oriented in a straight manner with respect to the shaft 18 to be a neutral position (reference position), the tilting operation of the distal end working unit 14 includes a movement range to a plus side (right side) and to a minus side (left side), respectively. In the present embodiment, the distal end working unit 14 has a movable range of +70° to −70° in relation to the tilting operation.

The proximal end part of the pull wire 70 is connected to a distal end part of a pull rod 91 (see FIG. 2). The pull wire 70 and the pull rod 91 are capable of relative rotation in the interior of a hollow shaft 89 (see FIG. 2) that is connected to the proximal end of the gear member 88, and are connected so as to transmit a tensile force in the direction of the proximal end of the pull rod 91 to the pull wire 70. Due to being constructed in this manner, when the pull rod 91 is displaced in the axial direction, the pull wire 70, which is connected to the pull rod 91, also is displaced in the axial direction to thereby carry out the opening and closing operation of the end effector 12. Further, when the distal end working unit 14 implements the rolling operation, since the pull wire 70 can rotate with respect to the pull rod 91, the rolling operation of the distal end working unit 14 is not hindered, twisting of the pull wire 70 does not occur, and damage to the pull wire 70 can be prevented.

As shown in FIG. 2, the pull rod 91 is inserted through the interior of the hollow shaft 89, and the proximal end thereof projects outwardly from the proximal end of the hollow shaft 89. On the other hand, at a distal end part thereof, the lever 24 is connected so as to be capable of swinging with respect to the body portion 23, at a location near the distal end of the body portion 23. A distal end of a lever rod 96 is connected rotatably in the vicinity of the distal end of the lever 24. The lever rod 96 is arranged below the body portion 23 substantially in parallel with the longitudinal direction of the body portion 23. A hook holder 116 that supports a hook member 118 is fixed to a lower part of the body portion 23. A compression spring 98 is arranged between a distal end surface of the hook holder 116 and a distal end expanded diameter portion 96a of the lever rod 96. The compression spring 98 normally applies a biasing force to the lever rod 96 in the distal end direction. Consequently, by the elastic force of the compression spring 98, the lever, which is connected to the lever rod 96, normally receives a force in a direction to open with respect to the body portion 23. A driving force from the lever is transmitted through an intermediate transmission mechanism to the opening and closing drive transmission member 80.

In the handle main body 20, a condition in which the lever 24 is open with respect to the body portion 23 (see FIG. 2) is regarded as an initial position. In the initial position, the pull rod 91 is advanced to a position at which the end effector 12 is in a fully open state. When the user grips the lever 24 and pulls the lever 24 toward the side of the body portion 23 (thereby closing the lever 24), the lever rod 96 is displaced in the direction of the proximal end. At this time, since the pull rod 91 is pulled in the direction of the proximal end through the intermediate force transmission mechanism, the end effector 12 is operated in a direction to close.

Next, primarily with reference to FIGS. 2 and 5, a mechanism will be described in relation to the rolling operation of the distal end working unit 14. In the present embodiment, the rolling operation of the distal end working unit 14 is carried out by transmitting a driving force of the motor 38 to the distal end working unit 14. A rolling operation drive system for causing the distal end working unit 14 to undergo a rolling operation comprises the aforementioned motor 38, the drive gear 40 that is fixed to the motor 38, the driven gear 128 that is enmeshed with the drive gear 40, a rolling drive transmission pipe 130 that is fixed to the driven gear 128, the bevel gear 86 that is enmeshed with the distal end of the rolling drive transmission pipe 130, and the rotating sleeve 56 that is enmeshed with the bevel gear 86. In the present embodiment, the rolling drive transmission pipe 130 is constituted by the gear member 88 and the hollow shaft 89. Further, the rotating drive transmission member 132, which transmits the rotary driving force from the handle 16 to the distal end working unit 14, is constituted from the rolling drive transmission pipe 130, the bevel gear 86, and the rotating sleeve 56.

The drive unit 22 is mounted on the handle main body 20, and in a state in which the controller 44 is connected to a power source, when the rolling switch 28 shown in FIG. 1 is operated by pressing, the motor 38 rotates, and a driving force from the motor 38 is transmitted to the distal end working unit 14 through the drive gear 40, the driven gear 128, the rolling drive transmission pipe 130, the bevel gear 86, and the rotating sleeve 56. As a result, a rolling operation of the distal end working unit 14 is carried out.

With the medical manipulator 10, transmission of the rotational force from the handle 16 to the side of the distal end working unit 14 is not carried out through a wire and a pulley, but rather is carried out through the rolling drive transmission pipe 130. Therefore, the distal end working unit 14 can be operated to roll over an unlimited range of rotation. Further, because the opening and closing drive transmission member 80 (the pull wire 70 and the pull rod 91) are inserted through the rolling drive transmission pipe 130, the opening and closing driving force can be transmitted appropriately to the end effector 12 without being influenced by rotation of the rolling drive transmission pipe 130.

Furthermore, as shown in FIG. 5, since the portion (the pull wire 70) of the opening and closing drive transmission member 80 corresponding to the joint 17 is flexible, with a simple structure, the opening and closing driving force can be transmitted appropriately to the end effector 12. Accordingly, without increasing the complexity of the mechanism of the distal end working unit 14, a structure can be maintained that enables the opening and closing operation as well as the tilting operation of the distal end working unit 14, while also realizing a rolling operation having an unlimited range of rotation.

Next, a mechanism related to the tilting operation of the distal end working unit 14 will be described. In the interior of the handle main body 20, there are provided a worm gear 144 that rotates about a vertical axis in conjunction with rotation of the tilt wheel 26, and a rotating body 146, having a worm wheel 147 that meshes with the worm gear 144, and which is capable of rotating about a lateral axis of the body portion 23.

The rotating body 146 includes the worm wheel 147 and a drive pulley 148, which are disposed coaxially. The worm wheel 147 and the drive pulley 148 rotate together in unison. The wire 150 is trained around the drive pulley 148, and the wire 150 is inserted into the shaft 18 and further is trained around the driven pulley 90 (see FIG. 5) at the distal end side of the shaft 18.

A first intermediate pulley 152 and a second intermediate pulley 154 are arranged, forwardly of the drive pulley 148 in the handle main body 20, with the wire 150 being trained around the first intermediate pulley 152 and the second intermediate pulley 154. A first tension pulley 159 and a second tension pulley 165 are arranged rearwardly of the drive pulley 148. The wire 150 also is trained around the first tension pulley 159 and the second tension pulley 165. A tensile force is applied to one side portion of the wire 150 between the drive pulley 148 and the driven pulley 90 by the first tension pulley 159. A tensile force also is applied to the other side portion of the wire 150 between the drive pulley 148 and the driven pulley 90 by the second tension pulley 165.

An annular space that extends along the axis of the shaft 18 exists between the shaft 18 and the rolling drive transmission pipe 130, and the wire 150 is inserted through the annular space. As discussed above, the wire 150 is trained around the driven pulley 90 (see FIG. 5), which is arranged at the distal end of the shaft 18.

The rotating operation, which is carried out manually by the tilt wheel 26 shown in FIGS. 1 and 2, and the operating force thereof are transmitted to the rotating body 146. The rotational force transmitted to the rotating body 146 drives the wire 150, which is trained around the drive pulley 148 provided on the rotating body 146. Driving of the wire 150 is output at the distal end of the shaft 18 to rotate the driven pulley 90, whereby the tilting operation with respect to the shaft 18 of the distal end working unit 14 is carried out.

In accordance with the medical manipulator 10 according to the present embodiment described above, the operating means 21 (see FIG. 5) that actuates the end effector 12 can be arranged substantially in the center of the distal end working unit 14, by having the rotating sleeve 56 (distal end side rotating body) be of a hollow shape. Thus, a structure can be realized in which the range of rotation of the rolling operation of the distal end working unit 14 is unlimited. With the present embodiment, since the opening and closing drive transmission member 80 transmits a driving force for driving the end effector 12 to open and close, and affects a mechanical action on the end effector 12, the opening and closing drive transmission member 80 constitutes the above-described operating means 21.

Further, since the distal end side fulcrum block 58 (rotating support cylinder) is arranged not on the inside of the rotating sleeve 56 but on the outer side thereof, the hollow portion of the rotating sleeve 56 can suitably ensure an arrangement space for the operating means 21, together with enabling the structure of the distal end working unit 14 to be simplified. Accordingly, in the present invention, a medical manipulator 10 is provided, which is equipped with the distal end working unit 14 having a high degree of freedom, without increasing the complexity of the structure of the medical manipulator 10.

In the present embodiment, the distal end side fulcrum block 58 is capable of rotating centrally about the tilt axis Oy that intersects the axis of the shaft 18 on the distal end of the shaft 18. Further, a pair of joint pins 73, 74, which are disposed on the tilt axis (Oy), are provided at the joint 17 between the shaft 18 and the distal end working unit 14, and the operating means 21 is inserted through a gap provided between the pair of joint pins 73, 74. According to this structure, the arrangement space for the operating means 21 can easily be assured in the interior of the joint 17.

In the case of the present embodiment, as shown in FIG. 4, the distal end side fulcrum block 58 that constitutes the rotating support cylinder is made up from the upper block 71 and the lower block 72 (a plurality of segments), which rotatably support the rotating sleeve 56 on the inside thereof, as a result of being connected together in the circumferential direction. More specifically, the upper block 71 and the lower block 72 are connected in the circumferential direction, whereby the distal end side fulcrum block 58 is constructed, which supports the rotating sleeve 56 on an inner circumferential portion thereof. Consequently, during assembly of the distal end working unit 14, by mutually joining the upper block 71 and the lower block 72 by welding or the like so that the rotating sleeve 56 is surrounded by the upper block 71 and the lower block 72, a configuration can easily be constructed in which the rotating body is arranged inside of the upper block 71 and the lower block 72, and a rotary support member is provided on the outer side.

In the medical manipulator 10 according to the present embodiment, the rolling operation is effected by an electrical drive provided through the motor 38, and the tilting operation is effected by a manual drive. However, in a modification of the medical manipulator 10, conversely, a configuration may be adopted in which the tilting operation is effected by an electrical drive provided through the motor 38, and the rolling operation is effected by a manual drive. In this manner, since a structure is provided in which either one of the tilting operation and the rolling operation is set into motion by the drive source, and both the tilting operation and the rolling operation are not effected by an electrical drive, compared to a structure in which both the tilting operation and the rolling operation are carried out by electrical drives, a reduction in size and weight by one of the drive sources can be realized.

According to another modification of the medical manipulator 10, among the tilting operation, the rolling operation, and the opening and closing operation, any one or two or more of these operations may be constituted as an electrically driven operation, or alternatively the tilting operation, the rolling operation, and the opening and closing operation may all be constituted as manually driven operations.

Second Embodiment

Figure 7:
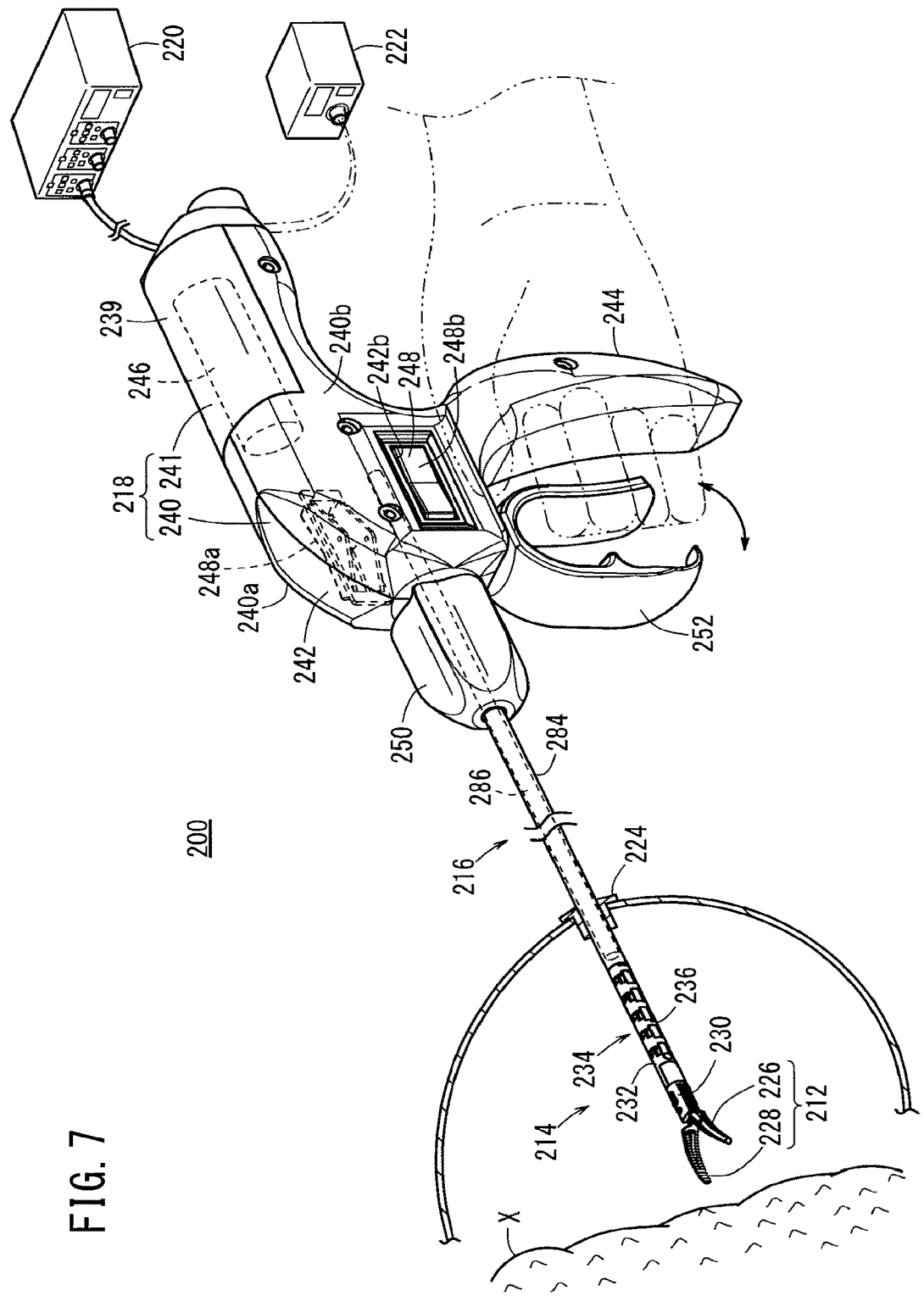
FIG. 7 is a perspective view with partial omission of a medical manipulator according to a second embodiment of the present invention.

FIG. 7 is a perspective view with partial omission of a medical manipulator 200 according to a second embodiment of the present invention. The medical manipulator 200 is used in an endoscopic surgical procedure, and is constructed so as to carry out a predetermined process (e.g., cauterization by application of heat) by applying electrical energy to a biological tissue that serves as a surgical target X to be treated. As a biological tissue that serves as the surgical target X, for example, tumors (lesions), muscles, blood vessels, or nerves, etc., may be cited as examples thereof. More specifically, the end effector 212 of the medical manipulator 200 is constituted as an end effector 212 (electric scalpel) that applies electrical energy to the biological tissue by gripping the biological tissue.

As shown in FIG. 7, the medical manipulator 200 comprises a distal end working unit 214 having an end effector 212 for carrying out a surgical procedure on a biological tissue, a shaft 216 connected to a proximal end side of the distal end working unit 214 and which extends a predetermined length (e.g., on the order of 350 mm) in the direction of the proximal end, and a handle 218 disposed on the proximal end side of the shaft 216, and which operates the distal end working unit 214 based on an operation (input) from a person or user of the medical manipulator 200. A controller 220 is connected to the handle 218 for supplying electrical power for effecting a predetermined operation of the distal end working unit 214. In addition, a high frequency power source 222 for energizing the end effector 212 with high frequency current is connected to the handle 218.

Upon use of the medical manipulator 200, the handle 218 is gripped and operated by the user (an operator such as a doctor or the like), and the distal end working unit 214 and the shaft 216, which constitute the distal end side of the medical manipulator 200, are inserted into the body of a patient. At this time, the user opens a small diameter hole at a predetermined position on the body surface of the patient, installs a trocar 224 together with injecting a carbon gas, and inserts the shaft 216 into the patient via the trocar 224. Further, in a state in which the distal end side of the medical manipulator 200 is inserted into the body, while observations are made through an endoscope, variations in posture and opening and closing operations of the end effector 212 are carried out appropriately. Consequently, the end effector 212 is delivered to the site of the biological tissue, and a procedure is performed to supply electrical current to the biological tissue.

The structure of the end effector 212 is not limited to an electric scalpel that supplies current to the biological tissue, and various alternative structures may be adopted for the end effector 212. For example, as the end effector 212, there may be applied a scissors or a knife (blade) for cutting biological tissue. Further, the end effector 212 may be constituted as a gripping device for gripping a medical device such as a forceps, a needle or the like, whereby a surgical procedure can be performed on the biological tissue using the medical device that is gripped.

The posture of the distal end working unit 214 including the end effector 212 can be changed at a plurality of degrees of freedom with respect to the shaft 216. With the present embodiment, the distal end working unit 214 can carry out a "tilting operation" (swinging operation) in which the distal end working unit 214 is operated to tilt in left and right directions with respect to the axis of the shaft 26, and a "rolling operation" in which the distal end working unit 214 is rotated about the axis in the longitudinal direction of the distal end effector 212. In the present embodiment, although the tilting operation of the distal end working unit 214 is a yaw operation for carrying out swinging movements in left and right directions, instead of a yaw operation, a pitch operation may be implemented in which upward and downward swinging movements are carried out.

The shaft 216 that is connected to the distal end working unit 214 extends in a straight line, and the handle 218 is connected to a proximal end portion of the shaft 216. The shaft 216 is an oblong and small diameter tubular member. A plurality of members configured to make up a power transmission mechanism are inserted into or are arranged in a hollow portion of the shaft 216. Such a power transmission mechanism transmits, from the handle 218 to the distal end working unit 214, power that is necessary for carrying out the opening and closing operation of the end effector 212, and the rolling operation and the tilting operation of the distal end working unit 214. During the surgical procedure, the proximal end side of the shaft 216 is exposed outside the body of the patient, and by manipulating the position and angle of the medical manipulator 200 from the outside, the insertion angle and insertion amount of the distal end working unit 214 and the shaft 216 that are inserted into the body are changed.

The handle 218 includes a handle main body 240 including a plurality of operating units, and which is formed in the shape of a pistol for enabling easy gripping thereof by one hand of the user, and a drive unit 241 including a motor 246 that is capable of being attached to and detached from the handle main body 240. When the motor 246 is driven in a state in which the drive unit 241 is mounted on the handle main body 240, a driving force from the motor 246 is transmitted to the distal end working unit 214. Thus, the form of use of the medical manipulator 200 can be one in which, concerning a manipulator main body thereof, which includes the handle main body 240, the shaft 216, and the distal end working unit 214, the manipulator main body can be discarded after being used a predetermined number of times, whereas the drive unit 241 can be used repeatedly many times by changing the manipulator main body that is connected to the drive unit 241.

The handle main body 240 includes a body portion 242, which extends in the same direction as the axial direction of the shaft 216, and a gripping unit 244 that extends downwardly from a lower side of the body portion 242. An internal space (not shown) of a comparatively large volume is formed inside a casing of the handle main body 240. Multiple drive components such as gears, links and the like, for effecting operations (a tilting operation, a rolling operation, an opening and closing operation) of the above-described distal end working unit 214 are disposed in the internal space. Further, a trigger 252 (opening and closing operating unit) for opening and closing the end effector 212, a switch 248 (tilting operation unit) for performing a tilting operation, and a rotating handle 250 (rolling operation unit) for performing a rolling operation, are disposed on the body portion 242.

The gripping unit 244 is formed somewhat more toward the distal end side than a middle region in the axial direction of the body portion 242, and has a structure such that, in a condition in which a user grips the gripping unit 244 with one hand, the switch 248, the rotating handle 250, and the trigger 252 can be operated by a finger of the one hand that has gripped the gripping unit 244.

The trigger 252 is disposed in front of the gripping unit 244 on a lower side of the body portion 242. The opening and closing operation of the end effector 212 is implemented by the user manually operating the trigger 252 of the handle 218. In other words, according to the present embodiment, the trigger 252 is constructed as a manual manipulating part, in which an opening and closing operation of the end effector 212 is carried out by mechanically transmitting to the end effector 212 of the distal end working unit 214 an operating force applied with respect to the trigger 252. More specifically, a structure is provided in which the end effector 212 is opened when the trigger 252 is moved forward, and the end effector 212 is closed when the trigger 252 is moved to the rearward side.

The switch 248 is provided on both side surfaces of the body portion 242. In the present embodiment, the switch 248 is constituted as an electrical manipulating part, which supplies an operating command to the motor 246 through a controller 220. The switch 248 is made up from a right side switch 248a, which is disposed on the right side of the handle main body 240, and a left side switch 248b, which is disposed on the left side of the handle main body 240. Central portions of the right side and the left side switches 248a, 248b are supported on the handle main body 240, and a structure is provided such that both end portions (a distal end portion and a proximal end portion) thereof can be displaced about the center portions, by the user pressing and operating the switches. When the right side switch 248a or the left side switch 248b is pressed and operated, a signal responsive to the pressed position is transmitted to the controller 220, and under a control action of the controller 220 the motor 246 drives, the driving force of the motor 246 is transmitted to the distal end working unit 214, whereby the distal end working unit 214 is tilted (laterally to the left and right, or vertically up and down) in a non-parallel direction with respect to the axis of the shaft 216.

In the present embodiment, the distal end working unit 214 is tilted to the right when a rearward part of the right side switch 248a is pressed or when a frontal part of the left side switch 248b is pressed, and the distal end working unit 214 is tilted to the left when a frontal part of the right side switch 248a is pressed or when a rearward part of the left side switch 248b is pressed. Owing to such a structure, in the event that either one of the right side switch 248a or the left side switch 248b is operated, since the feeling of operation of the switch 248 matches with the sense (viewpoint) of the user, excellent operability is achieved.

The rotating handle 250 is disposed in surrounding relation to the proximal end side of the shaft 216 at a portion where the shaft 216 is connected to the distal end side of the body portion 242. The rolling operation is implemented by the user manually operating the rotating handle 250. In other words, in the present embodiment, the rotating handle 250 is constituted as a manual operating unit. When the rotating handle 250 is operated by being rotated, the operating force applied thereto is transmitted mechanically to the distal end working unit 214 through a tilting operation power transmission system, which is disposed internally in the handle 218 and the shaft 216, whereupon the distal end working unit 214 is rotated about the longitudinal axis of the distal end working unit 214. Thus, according to the present embodiment, when the rotating handle 250 is manipulated to rotate in a clockwise direction, the distal end working unit 214 rotates clockwise, whereas when the rotating handle 250 is manipulated to rotate in a counterclockwise direction, the distal end working unit 214 rotates counterclockwise.

The drive unit 241 includes a housing 239, a motor 246 disposed inside the housing 239, and a non-illustrated pinion gear, which is fixed to an output shaft of the motor 246. The drive unit 241 is detachable from the rear of the handle main body 240. Further, the aforementioned controller 220 and the high frequency power source 222 are connected to the drive unit 241. The controller 220 controls the supply of power and driving of the motor 246, and receives electrical power from an external power source. When the switch 248 is operated, a signal corresponding to the operation thereof is transmitted to the controller 220, and the controller 220 controls driving of the motor 246. Some or all of the functions of the controller 220 may be incorporated integrally in the drive unit 241. The high frequency power source 222 includes a function to supply power (high frequency voltage) to the end effector 212 based on manipulations performed by the user.

Figure 8:
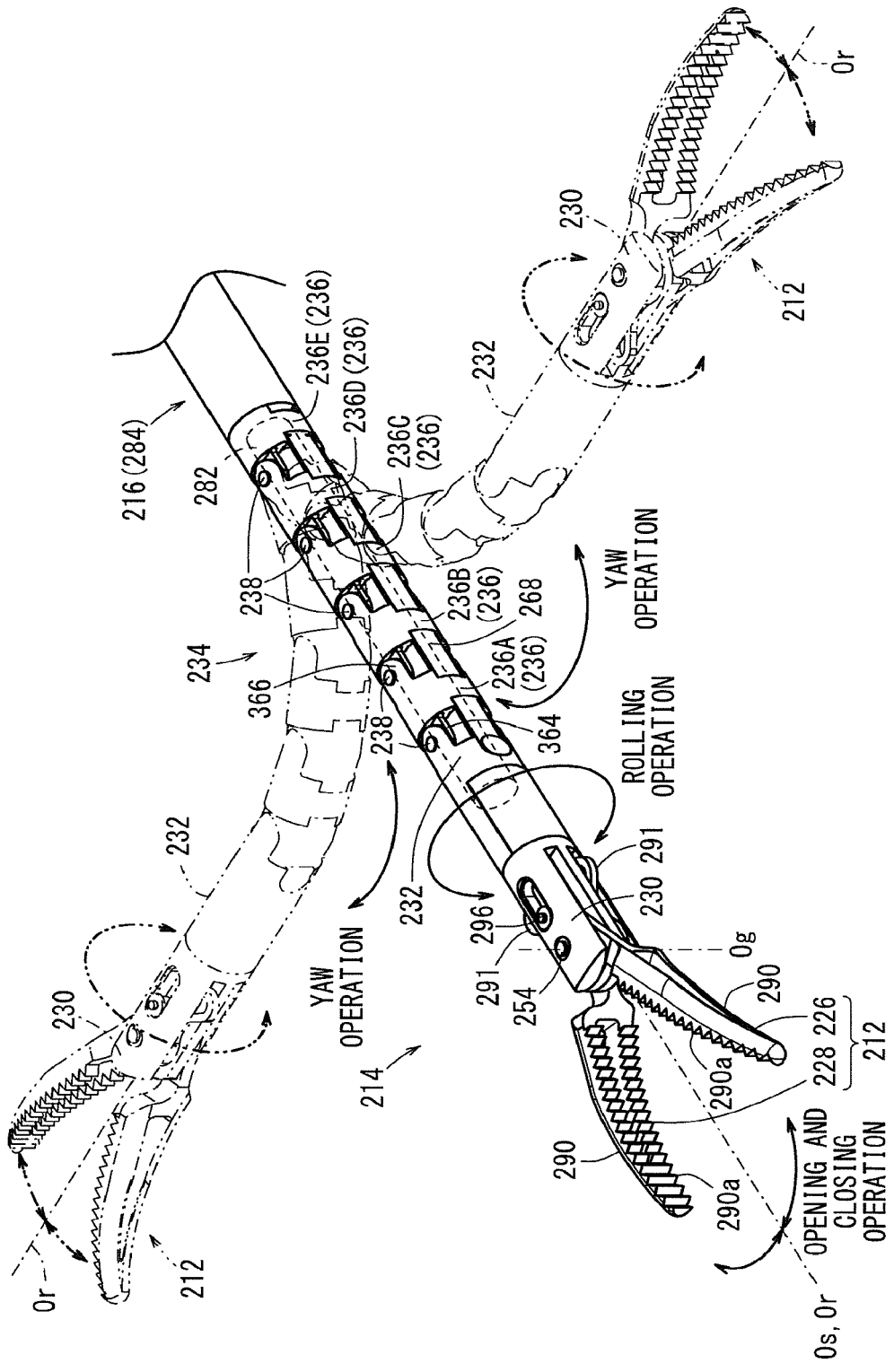
FIG. 8 is a partial perspective view showing an enlarged representation of the distal end working unit of the medical manipulator of FIG. 7.
Figure 9:
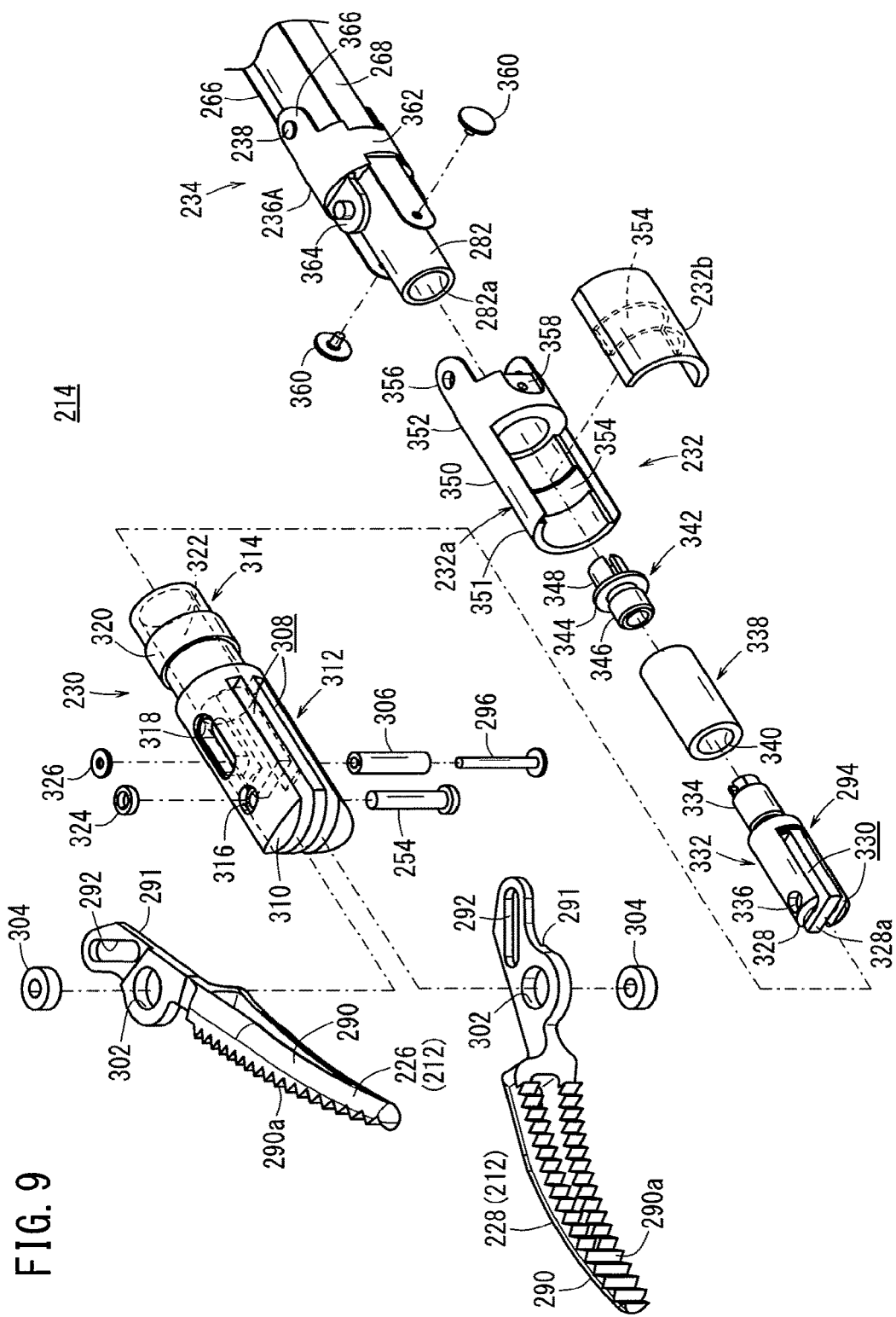
FIG. 9 is an exploded perspective view showing an enlarged representation of a distal end side of the medical manipulator of FIG. 7.
Figure 10:
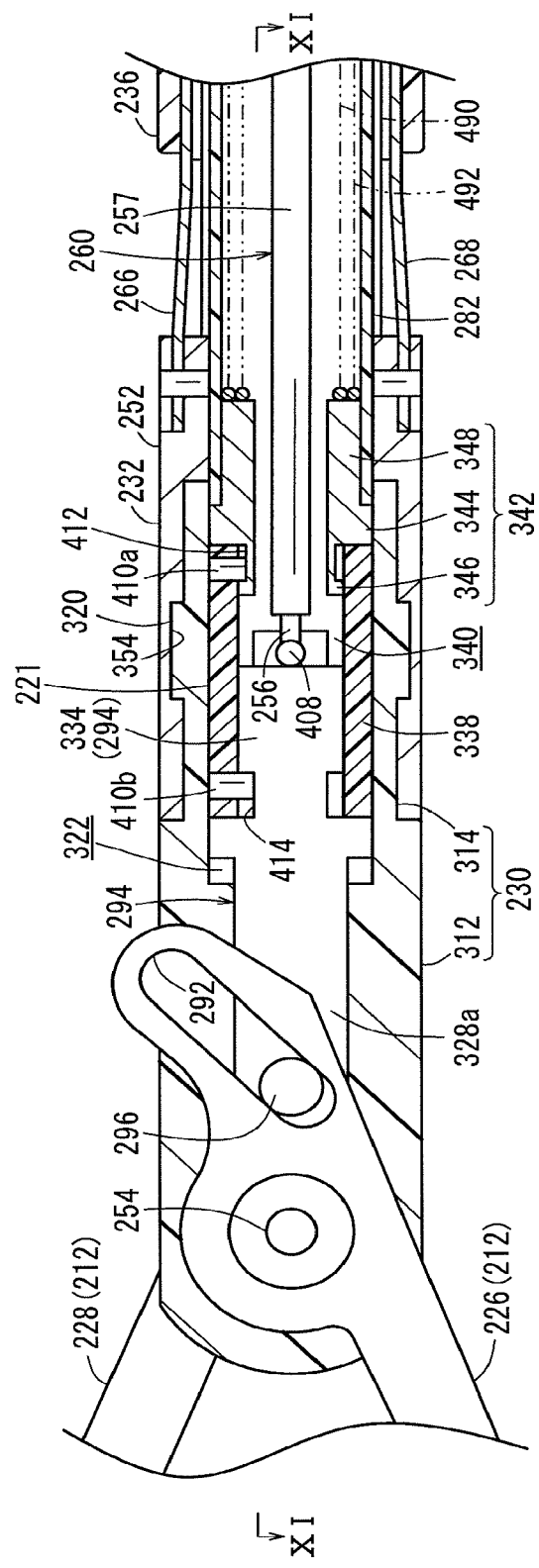
FIG. 10 is a vertical cross-sectional view showing the distal end working unit of the medical manipulator of FIG. 7.
Figure 11:
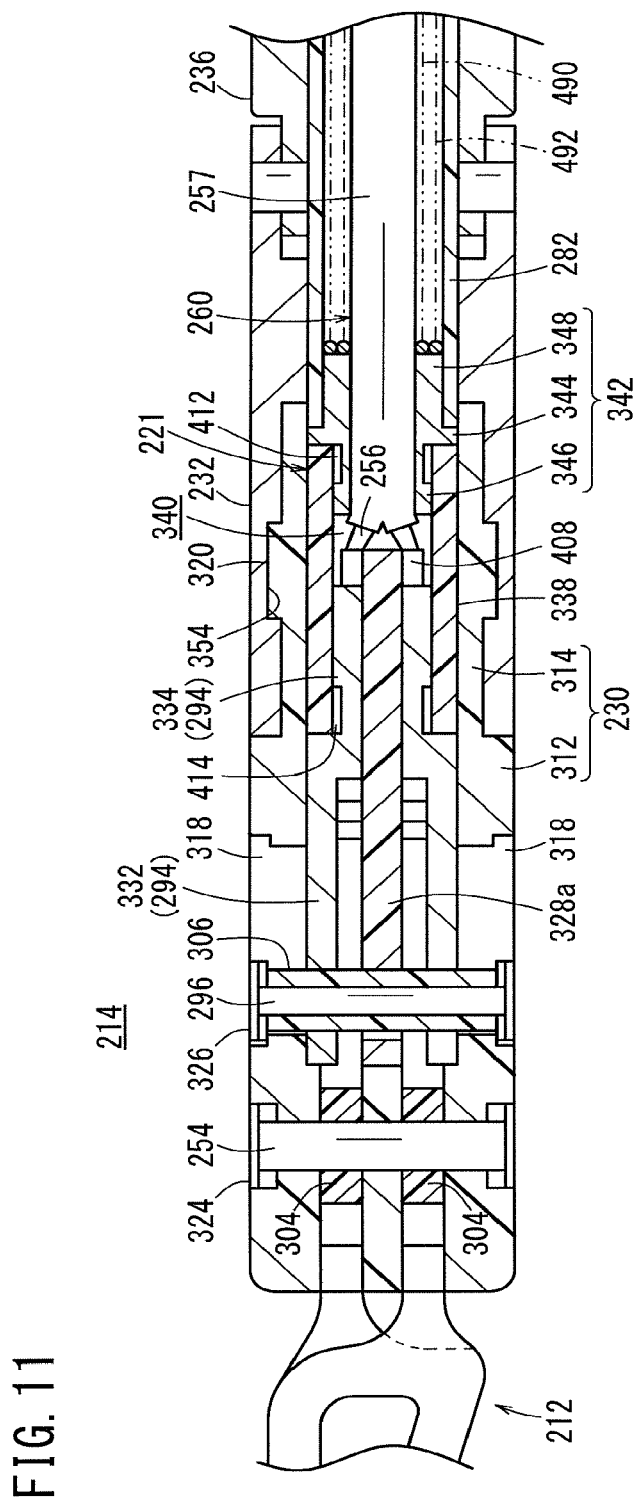
FIG. 11 is a cross sectional view taken along line XI-XI of FIG. 10.

FIG. 8 is a partial perspective view of the distal end working unit 214. FIG. 9 is an exploded perspective view of the distal end working unit 214. FIG. 10 is a vertical cross sectional view of the distal end working unit 214. FIG. 11 is a cross sectional view taken along line XI-XI of FIG. 10. As shown in FIGS. 8 through 11, the distal end working unit 214 includes the end effector 212 that is capable of being opened and closed, a gripper retaining member 230 (distal end side rotating body) to which the end effector 212 is fixed, an outer shell member 232 (rotary support tube) that rotatably supports the gripper retaining member 230 for axial rotation, a bending portion 234 that is bendably deformable between the shaft 216 and the outer shell member 232, and a hollow tube 282, which is arranged inside the bending portion 234.

The end effector 212 is made up from a first gripper member 226 and a second gripper member 228. The first gripper member 226 and the second gripper member 228 are connected by a fulcrum pin 254 so as to be capable of rotating about a gripper axis Og (see FIG. 8). The first and second gripper members 226, 228 include jaw members 290 having respective gripping surfaces, and flat plate-shaped extension pieces 291 that extend toward the proximal end from the jaw members 290. The jaw members 290 are of a shape that extends in the distal end direction while the distal end portions are bent downward, and serrated meshing teeth 290a are formed on mutually facing surfaces thereof. The meshing teeth 290a of the first and second gripper members 226, 228 mesh with one another in a closed state.

As shown in FIGS. 9 and 11, round holes 302 in which a fulcrum pin 254 is fitted are bored through the extension pieces 291 at a portion near the distal ends thereof. The fulcrum pin 254 is supported by insulating rings 304, which are fitted into the round holes 302. Elongate holes 292 are bored through the extension pieces 291 near the proximal ends thereof. A movable pin 296 is inserted through an insulating cylinder 306 in the elongate holes 292.

Two gaps 308 are formed in the gripper retaining member 230. The two gaps 308 extend mutually in parallel along the longitudinal direction of the gripper retaining member 230, and open on the distal end and on both side surfaces of the gripper retaining member 230. In a condition in which the respective extension pieces 291 of the first and second gripper members 226, 228 have been inserted in the gaps 308, the first and second gripper members 226, 228 are made rotatable about the fulcrum pin 254. The proximal end side of the gripper retaining member 230 is inserted rotatably through the cylindrically shaped outer shell member 232.

The gripper retaining member 230 is made up from a three-pronged gripper side section 312, which includes three retaining plates 310 that extend toward the distal end so as to form the above-described gaps 308, and an engagement cylinder 314, which extends toward the proximal end and joins with the proximal end side of the three-pronged gripper side section 312.

Fulcrum pin holes 316 for insertion therein of the fulcrum pin 254 are formed in portions near the distal ends of the three retaining plates 310. In a condition in which the extension pieces 291 of the first and second gripper members 226, 228 are arranged in the gaps 308, the fulcrum pin 254 is inserted through the fulcrum pin holes 316, and the end of the fulcrum pin 254 is fixed by a bushing 324. Elongate movable pin holes 318 in which both ends of the movable pin 296 can be inserted are formed more toward the proximal end side than the fulcrum pin holes 316 in the three-pronged gripper side section 312. In a condition in which the movable pin 296 has been inserted through the elongate holes 292 provided in the first and second gripper members 226, 228, and the elongate movable pin holes 318 are provided in the gripper retaining member 230, the movable pin is capable of moving along the elongate holes 292, 318. A washer 326 is fixed to the end of the movable pin 296.

An annular projection 320, which projects diametrically outward and extends in the circumferential direction, is disposed on an outer surface of the engagement cylinder 314. Within the three-pronged gripper side section 312 and the engagement cylinder 314, a sliding space 322 through which a moving body 294 is inserted (see FIG. 10) is formed in a continuous manner.

The outer shell member 232 rotatably supports the gripper retaining member 230 on an inner circumferential portion thereof. The outer shell member 232 is made up from a plurality of segments, which rotatably support the engagement cylinder 314 of the gripper retaining member 230 inside thereof, as a result of being connected together in a circumferential direction. More specifically, as shown in FIG. 9, in the present embodiment, the outer shell member 232 is made up from a first block 232a (segment) having a semicircular portion 351 and a proximal end side cylindrical portion 352, and a semicircular second block 232b (segment). The first block 232a and the second block 232b are assembled together to form a hollow cylindrical shape.

Both end parts in the circumferential direction of the semicircular portion 351 of the first block 232a, and both end parts in the circumferential direction of the second block 232b are joined together by a suitable joining means, such as by welding or an adhesive or the like, whereby the first block 232a and the second block 232b are fixed mutually to one another. A hollow cylindrically shaped distal end side cylindrical portion 350 is constituted from the second block 232b and the semicircular portion 351 of the first block 232a. An annular groove 354, which extends once therearound, is disposed on an inner surface of the distal end side cylindrical portion 350. The width of the annular groove 354 is on the order of 2 mm, for example. By engagement of the projection 320 provided on the gripper retaining member 230 with the annular groove 354 provided in the outer shell member 232, the gripper retaining member 230 is supported rotatably on the inner side of the outer shell member 232, in a state in which axial movement of the gripper retaining member 230 with respect to the outer shell member 232 is restricted.

A moving body 294, which is capable of advancing and retracting with respect to the gripper retaining member 230, is arranged in the interior of the gripper retaining member 230. The movable pin 296 is fixed to the moving body 294. During the rolling operation, the gripper retaining member 230 and the moving body 294 rotate together, however, during the opening and closing operation, the gripper retaining member 230 does not move, and the moving body 294 makes advancing and retracting movements on the inner side of the gripper retaining member 230.

As shown in FIG. 9, the moving body 294, similar to the gripper retaining member 230, includes a three-pronged moving body side section 332, which includes three retaining plates 328 that extend toward the distal end so as to form gaps 330, and an insertion part 334, which extends toward the proximal end and joins with the proximal end side of the three-pronged moving body side section 332. Round holes 336 for the movable pin 296 and through which the movable pin 296 is inserted are formed in portions near the distal end side of the three retaining plates 328.

The retaining plate 328a, which extends in the center among the three retaining plates 328 of the moving body 294, is constituted by an insulating material. As shown in FIG. 11, the retaining plate 328a penetrates through the insertion part 334, and the proximal end thereof projects outwardly from the insertion part 334. On the retaining plate 328a, welded portions 408 are provided on both upper and lower surfaces of a part that projects from a proximal end of the insertion part 334. Metal wires 256, which are exposed from the distal end of a conductive line 260, are welded by a welding material to the welded portions 408. A distal end part of the conductive line 260 extends in the axial direction in the interior of the hollow tube 282, and is fixedly retained by a connector 342.

A cylindrical body 338 having a hollow cylindrical shape, and which is capable of moving in an axial direction with respect to the engagement cylinder 314, is arranged on the inner side of the engagement cylinder 314 of the gripper retaining member 230. The total length of the cylindrical body 338 is on the order of 6 mm, for example. The insertion part 334 of the aforementioned moving body 294 is inserted in a distal end portion of the cylindrical body 338. A connector 342 is inserted in a proximal end portion of the cylindrical body 338.

As shown in FIG. 10, connecting pins 410a, 410b, which project inwardly from the inner circumferential surface of the cylindrical body 338, are disposed on the distal end side and the proximal end side of the cylindrical body 338. The inner end of the connecting pin 410b that is disposed on the distal end side is inserted into a moving body side engagement groove 414, which is provided in the insertion part 334 of the moving body 294. The inner end of the connecting pin 410a that is disposed on the proximal end side is inserted into a connector side engagement groove 412, which is provided in the connector 342. By this structure, the connections in the axial direction between the connector 342, the cylindrical body 338, and the moving body 294 are reinforced by the connecting pins 410a, 410b, and the operating force of the advancing and retracting movements, which is transmitted from the hollow tube 282, is further transmitted reliably to the moving body through the cylindrical body 338.

The hollow cylindrical connector 342 is connected to the proximal end of the cylindrical body 338. The connector 342 includes a flange 344 disposed at an intermediate location in the longitudinal direction, a distal end connecting projection 346 that extends toward the distal end from the flange 344, and a proximal end connecting projection 348 that extends toward the proximal end from the flange 344. The distal end connecting projection 346 of the connector 342 is inserted into the cylindrical body 338, and the proximal end connecting projection 348 of the connector 342 is inserted into the hollow tube 282, thereby connecting the cylindrical body 338 and the hollow tube 282 to each other.

To the proximal end of the connector 342, there is connected a hollow tube 282, which includes a hollow portion 282a (see FIG. 9) that penetrates in the axial direction. The hollow tube 282 is flexible and is capable of following the bending movement of the bending portion 234. The hollow tube 282 is arranged inside the bending portion 234, and the proximal end thereof is connected and fixed to an inner tube 286 of the shaft 216 (see FIG. 12). The hollow tube 282 functions as a torque tube, which is capable of rotating even if the hollow tube 282 is bent in following relation to the bending movement of the bending portion 234. The inner diameter of the hollow tube is on the order of 1.5 mm, for example.

In the distal end working unit 214 which is constructed in this manner, movement in the axial direction of the hollow tube 282 is transmitted to the moving body 294 through the connector 342 and the cylindrical body 338. Additionally, in a position at which the moving body 294 is moved forward inside the gripper retaining member 230 (i.e., in a state in which the movable pin 296 is located on the distal end side of the elongate hole 292), the extension pieces 291 of the first and second gripper members 226, 228 intersect at the location of the movable pin 296. Therefore, the distal end portions of the first and second gripper members 226, 228 separate from one another and are placed in an open condition. In a position at which the moving body 294 is retracted inside the gripper retaining member 230 (i.e., in a state in which the movable pin 296 is located on the proximal end side of the elongate hole 292), accompanying guiding of the elongate holes 292 of the first and second gripper members 226, 228, and the respective extension pieces 291 coming into proximity (overlapping) with each other, the distal end portions of the first and second gripper members 226, 228 approach one another mutually and are placed in a closed condition. In this manner, at the end effector 212, an opening and closing operation is realized by transmission of the operating force in distal and proximal end directions from the hollow tube 282. The opening and closing operation can be realized at a desired timing based on operations of the user, regardless of any change in the posture of the end effector 212.

Figure 12:
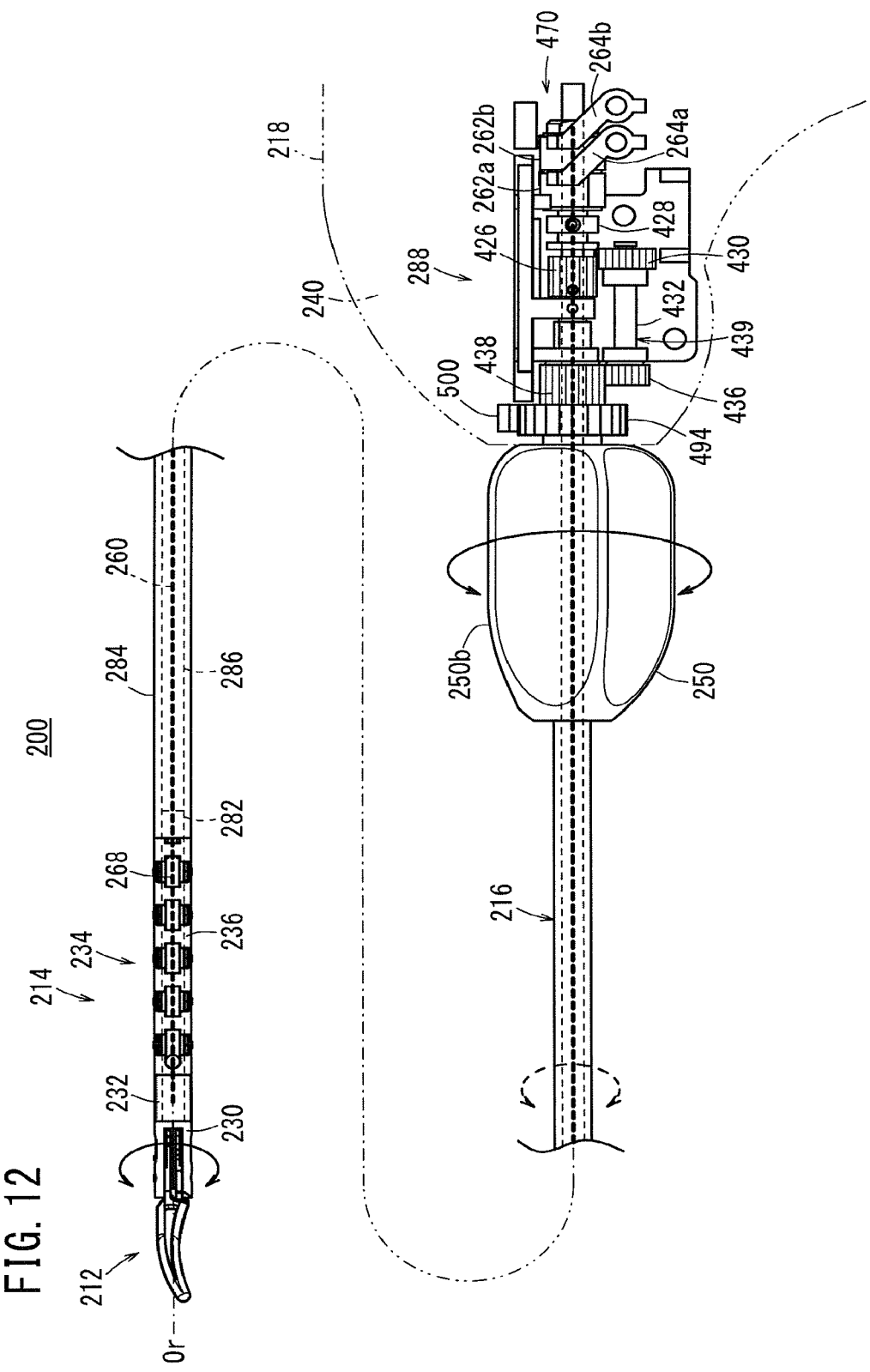
FIG. 12 is a schematic side view for describing a rolling operation of the medical manipulator of FIG. 7.

As shown in FIG. 12, the shaft 216 that is connected to the bending portion 234 is constituted by a double tube structure, including an outer tube 284, and an inner tube 286 that is disposed in the interior of the outer tube 284. The inner tube 286 is capable of moving in an axial direction and of rotating axially in the interior of the outer tube 284. The proximal end of the hollow tube 282 and the distal end of the inner tube 286 are connected to one another and are incapable of rotating relatively. Consequently, accompanying axial movement of the inner tube 286 in the axial direction in the interior of the outer tube 284, the hollow tube 282 moves in the axial direction inside of the bending portion 234. Further, accompanying rotation of the inner tube 286 about the axis in the interior of the outer tube 284, the hollow tube 282 rotates inside the bending portion 234.

A non-illustrated advancing and retracting movement mechanism is connected internally in the handle 218 at the proximal end side of the inner tube 286. The advancing and retracting movement mechanism includes a plurality of links, which mechanically connect the inner tube 286 with the trigger 252 (see FIG. 7). When the user performs a manual operation to pull the trigger 252, the operating force of the trigger 252 is transmitted to the proximal end side within the handle 218, and the inner tube 286 is moved in the direction of the proximal end through the advancing and retracting movement mechanism, whereby the hollow tube 282 is moved toward the proximal end. On the other hand, when the user performs a manual operation to push on the trigger 252, the operating force of the trigger 252 is transmitted to the proximal end side within the handle 218, and the inner tube 286 is moved in the direction of the distal end through the advancing and retracting movement mechanism, whereby the hollow tube 282 is moved toward the distal end.

The length in the axial direction of the hollow tube 282 is longer than the axial length of the bending portion 234 of the distal end working unit 214, such that even if the hollow tube 282 is advanced and retracted, the hollow tube 282 normally is arranged to overlap with the bending portion 234. Accordingly, even if the bending portion 234 is subjected to bending and the hollow tube 282 bends in following relation thereto, the hollow tube 282 can be advanced and retracted along the bend, and the operating force of the advancing and retracting movement can be transmitted to the cylindrical body 338 that is connected to the distal end side of the hollow tube 282.

Together with gripping of the biological tissue by the end effector 212, the medical manipulator 200 also includes a function to supply electrical current to the biological tissue. Therefore, the first and second gripper members 226, 228 shown in FIG. 7, etc., are made from a conductive material, and constitute electrodes (a minus terminal and a plus terminal) that supply current to the biological tissue. More specifically, the end effector 212 according to the present embodiment is a bipolar type of electric scalpel. The end effector 212 is not limited to such a structure, and may be constituted as a monopolar type of electric scalpel.

As shown in FIGS. 10 and 11, a conductive line 260 is connected to the proximal end of the moving body 294. The conductive line 260 is constituted from two metal wires 256 made of copper, for example, and an insulating material 257 that covers the two metal wires 256. The conductive line 260 extends toward the proximal end together with the shaft 216, and is inserted into the handle 218. In the present embodiment, the conductive line 260 is arranged to pass through the axial center of the hollow tube 282 and the inner tube 286. Consequently, since there is no need to provide separate wiring for the conductive line 260 on the side surface of the distal end working unit 214 or the shaft 216, entanglement of the conductive line 260 by operation of the distal end working unit 214 is avoided, and supply of current can suitably be performed.

As shown in FIG. 11, the first gripper member 226 and the second gripper member 228 are pivotally supported by one fulcrum pin 254 through the insulating rings 304. When the operating force of the opening and closing operation is received, the distal end parts of the first and second gripper members 226, 228 are made to approach and separate away from one another about the fulcrum pin 254. Therefore, although supply of current is interrupted in an open state in which the distal end parts of the first and second gripper members 226, 228 are separated, in a closed state in which the distal end parts of the first and second gripper members 226, 228 are brought into abutment (including an indirectly closed state upon sandwiching of a biological tissue), the first and second gripper members 226, 228 become energized to thereby supply electrical current to the biological tissue.

As discussed above, in the close state of the end effector 212, a current supplying condition is formed by the connection of the first and second gripper members 226, 228, which are of different polarities. More specifically, in a state in which a biological tissue is sandwiched between the first and second gripper members 226, 228, a high frequency current, which is supplied to the first and second gripper members 226, 228 through the conductive line 260 from the high frequency power source 222, is made to flow to the biological tissue, and a predetermined process (cauterization by application of heat) is performed on the biological tissue.

As shown in FIG. 12, a slip ring system 470 is disposed inside the handle main body 240, for continuously performing the electrical connection between the conductive line 260 and the high frequency power source 222 at the time that the inner tube 286 is rotated. The slip ring system 470 includes a pair of rotating terminals 262a, 262b, which are fixed to the inner tube 286 of the shaft 216 inside the handle main body 240, and a pair of contact terminals 264a, 264b, which are in contact, respectively, with the pair of rotating terminals 262a, 262b.

The one and the other of the rotating terminals 262a, 262b are connected electrically, respectively, to the one and the other of the two metal wires 256 in the conductive line 260. The rotating terminals 262a, 262b rotate together with the inner tube 286. The two contact terminals 264a, 264b are fixed in the handle, and are connected to the high frequency power source 222 (see FIG. 7) externally of the handle 218. With the slip ring system 470, even when the rotating terminals 262a, 262b are rotated, contact between the rotating terminals 262a, 262b and the contact terminals 264a, 264b is maintained, and the output from the high frequency power source 222 can be supplied to the end effector 212 through the conductive line 260.

As shown in FIGS. 10 and 11, a double coil (the first coil 490, the second coil 492) is arranged in the interior of the hollow tube 282. The first and second coils 490, 492 extend axially in an overlapping manner in a state of being wound mutually in different (clockwise and counterclockwise) winding directions. Consequently, when the hollow tube 282 is rotated clockwise, the coil (e.g., the first coil 490) that is wound in the clockwise direction expands in diameter, and the coil (e.g., the second coil 492) that is wound in the counterclockwise direction becomes reduced in diameter. Therefore, the shape of the double coil overall is maintained. As a result, in a state in which the hollow tube 282 is bent by the bending portion 234, the hollow tube 282 can easily be rotated, and a rotational torque can be transmitted to the distal end side (the end effector 212).

The rolling operation of the distal end working unit 214 is carried out by rotating the gripper retaining member 230 with respect to the outer shell member 232. The outer shell member 232 is connected in such a manner so as not to rotate with respect to the bending portion 234, whereas the gripper retaining member 230 is capable of being rotated with respect to the outer shell member 232. Therefore, the end effector 212 as well as the gripper retaining member 230 rotate together in unison.

As shown in FIG. 12, the inner tube 286 projects toward the proximal end more than the outer tube 284, and is supported rotatably by a rotation mechanism 288 in the interior of the handle 218. In the interior of the handle main body 240, there are provided a drive gear 438, which is fixed to the proximal end side of the rotating handle 250 and is rotatable integrally with the rotating handle 250, a driven gear 426, which is fixed to the inner tube 286 and is rotatable integrally with the inner tube 286, and an intermediate drive shaft 439 that carries out power transmission between the drive gear 438 and the driven gear 426. The intermediate drive shaft 439 includes a first intermediate gear 436, which is provided on one end side and is enmeshed with the drive gear 438, a second intermediate gear 430, which is provided on another end side and is enmeshed with the driven gear 426, and a connecting shaft 432 connected between the first intermediate gear 436 and the second intermediate gear 430. The intermediate drive shaft 439 is thus rotatably supported in the interior of the handle main body 240.

When the user manually performs a rotating operation on the rotating handle 250, the operating force (rotary driving force) thereof is transmitted to the inner tube 286 through the drive gear 438, the intermediate drive shaft 439, and the driven gear 426. Since the number of teeth of the driven gear 426 is less than the number of teeth of the drive gear 438, the inner tube 286 is rotated by a lesser amount of rotation than the amount of rotation of the rotating handle 250. The rotational force transmitted to the inner tube 286 is transmitted to the hollow tube 282. As a result, the gripper retaining member 230 and the end effector 212, which are connected to the distal end side of the hollow tube 282, are rotated about the roll axis Or (see FIG. 8). This operation is referred to as a rolling operation of the distal end working unit 214. In this case, the moving body 294, the cylindrical body 338, the connector 342, and the conductive line 260 also are rotated together with the gripper retaining member 230.

The inner tube 286 is rotatable in an unlimited manner with respect to the outer tube 284. The hollow tube 282, which is arranged at a position overlapping with the bending portion 234, also is rotatable in an unlimited manner. Similarly, the gripper retaining member 230 and the end effector 212 are rotatable in an unlimited manner. Further, since the conductive line 260 extends inside the hollow tube 282 and the inner tube 286, the hollow tube 282 and the inner tube 286 rotate together integrally. As a result, with the medical manipulator 200, the movable range (range of rotation of the end effector 212) of the rolling operation of the distal end working unit 214 is unlimited. Accordingly, a change in posture of the end effector 212 by the rolling operation can be carried out any number of times.

As shown in FIG. 12, a latch gear 494 that rotates together with the rotating handle 250 is disposed on the proximal end side of the rotating handle 250. The latch gear 494 further is arranged on a distal end in the interior space of the handle 218. The outer circumferential portion of the latch gear 494 is formed in a wavelike shape along the circumferential direction thereof, and a latching piece 500 abuts against the outer circumferential portion. When the latch gear 494 is rotated accompanying the rotating operation of the rotating handle 250, owing to the wavelike shape of the outer circumferential portion of the latch gear 494, the latching piece 500 swings while undergoing elastic deformation. Along with displacement of the latching piece 500 at this time, since vibration and operating noise is generated, the operational feeling of the rotating handle 250 can be recognized by the user.

The tilting operation of the medical manipulator 200 is realized by the bending portion 234 that is connected to the proximal end side of the outer shell member 232. The bending portion 234 is constituted by juxtaposing in the axial direction a plurality of joint members 236 (five are shown in FIG. 12), which are made of a hard material. Although the joint members 236 are constituted from stainless steel, insofar as they are excellent in durability and are capable of realizing the functions of the present invention, the joint members 236 are not limited to being made from stainless steel, and for example, may be made from a hard resin, such as a polyether ether ketone (PEEK) resin or the like. Hereinbelow, a description will be given in which the letters A through E are appended to each of the respective joint members 236 in order from the distal end side.

As shown in FIGS. 8 and 9, four of the joint members 236A through 236D from among the five joint members 236A through 236E that make up the bending portion 234 are each equipped with a center cylindrical portion 362 (cylindrical portion), which is formed in a cylindrical shape in a central region thereof, a distal end hinge piece 364, which extends toward the distal end side from the center cylindrical portion 362, and a proximal end hinge piece 366, which extends toward the proximal end side from the center cylindrical portion 362.

The distal end hinge piece 364 is formed to extend inwardly more than the proximal end hinge piece 366. The adjacent joint members 236 are connected so as to be mutually rotatable about hinge shafts 238, in a state in which the distal end hinge pieces 364 and the proximal end hinge pieces 366 overlap one another. As shown in FIGS. 9 and 11, at upper and lower positions of the proximal end side cylindrical portion 352 of the outer shell member 232, outer shell member side hinge pieces 356 are formed, which project in the proximal direction. The outer shell member side hinge pieces 356 are connected rotatably to the joint member 236A on the furthest most distal end side.

The joint member 236E on the furthest most proximal end side is connected and fixed to the distal end of the shaft 216. Although the joint member 236E on the furthest most proximal end side includes the center cylindrical portion 362 and the distal end hinge piece 364 in the same manner as the joint members 236A through 236D, the joint member 236E is not provided with the proximal end hinge piece 366 on the proximal end side of the center cylindrical portion 362. With the proximal end thereof being fitted into the outer tube 284, the joint member 236E is connected and fixed to the outer tube 284.

On both sides of the five joint members 236 that are arrayed in the axial direction, a pair of belts (a first belt 266 and a second belt 268) are inserted along the bending portion 234. The respective joint members 236 are retained slidably by the first and second belts 266, 268. As shown in FIG. 9, cutout portions 358, which match substantially with the distal end shapes of the first and second belts 266, 268, are formed as a pair on the outside surface of the proximal end side cylindrical portion 352. The distal ends of the belts are connected and fixed in the cutout portions 358 by fixing pins 360.

In the medical manipulator 200 that is constructed in the foregoing manner, based on a rotational drive of the motor 246, a driving force is transmitted to the first belt 266 and the second belt 268, whereby the first belt 266 is advanced or retracted with respect to the bending portion 234, and the second belt 268 is retracted or advanced with respect to the bending portion 234. More specifically, by the motor 246 being driven and rotated, the driving force thereof is transmitted to the first belt 266 and the second belt 268 via a tilting power transmission mechanism, which is disposed inside the handle 218 and the shaft 216. Although the structure of the tilting power transmission mechanism is not shown, a structure may be implemented in which the rotational drive of the motor 246 is converted into a linear drive, for example, by a rack and pinion mechanism. Alternatively, in a tilting power transmission mechanism of another structure, a mechanism employing pulleys, belts, wires or the like may be used.

As a result of the driving force of the motor 246 being transmitted to the first belt 266 and the second belt 268, the first belt 266 and the second belt 268 are moved in mutually opposite directions in relation to the direction in which the bending portion 234 extends. In the case that the first belt 266 is retracted and the second belt 268 is advanced with respect to the bending portion 234, the bending portion 234 bends to the right, accompanied by the outer shell member 232 that is connected to the distal end side of the joint member being oriented in a rightward direction. In the case that the first belt 266 is advanced and the second belt 268 is retracted with respect to the bending portion 234, the bending portion 234 bends to the left, accompanied by the outer shell member 232 that is connected to the distal end side of the joint member 236A being oriented in a leftward direction. The belts are not limited to the structure described above, in which a pair (two) of such belts are disposed on the bending portion 234, and one or three or more of such belts may be provided.

The yaw operation of the distal end working unit 214 is implemented by continuing to bend in an interlocked manner the five hinge shafts 238 about the operational support point of the joint member 236E. Stated otherwise, by the outer shell member 232 and the joint members 236A through 236D being inclined at substantially the same angle, the end effector 212 and the gripper retaining member 230 on the distal end side of the bending portion 234 are tilted integrally. Although the movable range of the tilting operation of the bending portion 234 can be set appropriately, if the movable range is set to a range at which the roll axis Or of the end effector 212 becomes perpendicular to the axis Os of the shaft 216, i.e., a range in which the end effector 212 can be tilted to the left and right by 180°, the facing orientation of the end effector 212 can be varied over a wide range within the body.

As has been described above, in the medical manipulator 200 according to the present embodiment, the rotational driving force on the side of the handle 218 is transmitted to the end effector 212 through the flexible hollow tube 282 that is disposed on the inner side of the bending portion 234, whereby the end effector 212 can be operated through an unlimited range of rotation. Therefore, the posture (angle) around the roll axis Or of the end effector 212 on the distal end side of the bending portion 234 can be changed freely, and the orientation of the end effector 212 can be changed any number of times to conform with the biological tissue, and to enable an accurate treatment to be applied to the biological tissue.

In accordance with the medical manipulator 200, the operating means 221 (see FIGS. 10 and 11) that serves to actuate the end effector 212 can be arranged substantially in the center of the distal end working unit 214, by having the gripper retaining member 230 (distal end side rotating body) be of a hollow shape. Thus, a structure can be realized in which the range of rotation of the rolling operation of the distal end working unit 214 is unlimited. Further, in the present embodiment, the moving body 294, the cylindrical body 338, the connector 342, the hollow tube 282, and the conductive line 260 exert operations mechanically or electrically with respect to the end effector 212. Accordingly, with the present embodiment, the operating means 221 that operates the end effector 212 is constituted by such members.

In the case of the present embodiment, since the outer shell member 232 (rotating support cylinder) is arranged not on the inside of the gripper retaining member 230 but on the outer side thereof, the hollow portion of the gripper retaining member 230 can suitably ensure an arrangement space for the operating means, together with enabling the structure of the distal end working unit 214 to be simplified. Accordingly, in the present embodiment, a medical manipulator 200 is provided, which is equipped with the distal end working unit 214 having a high degree of freedom, without increasing the complexity of the structure of the medical manipulator 200.

In the case of the present embodiment, the outer shell member 232 that constitutes the rotating support cylinder is made up from the first block 232a and the second block 232b (a plurality of segments), which rotatably support the rotating sleeve on the inside thereof, as a result of being connected together in the circumferential direction. More specifically, the first block 232a and the second block 232b are connected in the circumferential direction, whereby the outer shell member 232 is constructed, which supports the rotating sleeve on an inner circumferential portion thereof. Consequently, during assembly of the distal end working unit 214, by mutually joining the first block 232a and the second block 232b by welding or the like, so that the gripper retaining member 230 is surrounded by the first block 232a and the second block 232b, a configuration can easily be constructed in which the rotating body is arranged inside of the first block 232a and the second block 232b, and a rotary support member is provided on the outer side of the rotating body.

In particular, in the present embodiment, by disposing the conductive line 260 in the hollow portion 282a of the hollow tube 282, a conductive path leading to the end effector 212, which is constituted as a bipolar type of electric scalpel, can easily be constructed, and electrical power can be supplied stably to the end effector 212. When the gripper retaining member 230 and the end effector 212 are rotated, rotation thereof takes place integrally with the conductive line 260 that is accommodated in the hollow tube 282, and therefore, disconnection of the end effector 212 and the conductive line 260 (conductive path) can reliably be prevented.

In the medical manipulator 200 according to the present embodiment, the tilting operation is effected by an electrical drive provided through the motor 246, and the rolling operation is effected by a manual drive. However, in the medical manipulator 200, conversely, a configuration may be adopted in which the rolling operation is effected by an electrical drive provided through the motor 246, and the tilting operation is effected by a manual drive. According to another modification of the medical manipulator 200, among the tilting operation, the rolling operation, and the opening and closing operation, any one or two or more of these operations may be constituted as an electrically driven operation, or alternatively the tilting operation, the rolling operation, and the opening and closing operation may all be constituted as manually driven operations.

Although certain preferred embodiments of the present invention have been shown and described in detail above, it should be understood that various changes and modifications may be made to the embodiments without departing from the scope of the invention as set forth in the appended claims.

What is claimed is:

1. A medical manipulator comprising:
   a handle;
   a shaft that extends from the handle;
   a distal end working unit having an end effector, and which is connected while capable of being tilted with respect to the shaft, and further which is capable of undergoing a rolling operation; and
   a drive member extending between the handle and the distal end working unit, the drive member configured to actuate the end effector;
   wherein the distal end working unit includes a distal end side rotating body, which is capable of being rotated integrally with the end effector about a roll axis and further has a hollow cylindrical portion, and a rotating support cylinder, which is capable of being changed in posture with respect to an axial direction of the shaft, and rotatably supports the distal end side rotating body on an inner circumferential portion thereof;

wherein a portion of the drive member is disposed inside the distal end working unit;

wherein the rotating support cylinder is capable of rotating centrally about a tilt axis that intersects a central longitudinal axis of the shaft on the distal end of the shaft;

wherein a pair of joint pins, which are disposed on the tilt axis, are provided at a joint between the shaft and the distal end working unit; and wherein a first bevel gear is supported rotatably by a first joint pin of the pair of joint pins.

2. The medical manipulator according to claim 1, wherein another portion of the drive member is inserted through a gap provided between the pair of joint pins.

3. The medical manipulator according to claim 1, wherein the rotating support cylinder is made up from a plurality of segments, which rotatably support the distal end side rotating body inside thereof, as a result of being connected together in a circumferential direction.

4. The medical manipulator according to claim 1, wherein the pair of joint pins include a second joint pin, and the first joint pin is axially aligned with the second joint pin.

5. The medical manipulator according to claim 1, wherein teeth of the first bevel gear are enmeshed with teeth of a second bevel gear on a hollow cylindrical gear member, the drive member inserted internally through a hollow portion of the hollow cylindrical gear member.

6. A medical manipulator, comprising:
   a shaft having a central axis extending longitudinally between a proximal end and a distal end of the shaft;
   a handle connected to the proximal end of the shaft;
   a working unit connected to the distal end of the shaft, the working unit comprising:
      an end effector;
      a tilting support cylinder configured to tilt about a tilt axis that intersects the central axis of the shaft at the distal end of the shaft;
      a rotating body rotatably supported on an inner circumferential portion of the tilting support cylinder, the rotating body configured to rotate integrally with the end effector about a roll axis; and
   a pair of joint pins provided at a joint between the shaft and the working unit, each joint pin of the pair of joint pins defining a longitudinal axis aligned with the tilt axis;
   a pull wire extending between the handle and the working unit, the pull wire including a first portion thereof disposed inside the working unit, the pull wire configured to actuate the end effector;
   wherein a first bevel gear is supported rotatably by a first joint pin of the pair of joint pins.

7. The medical manipulator of claim 6, wherein a second portion of the pull wire extends through a gap provided between the pair of joint pins.

8. The medical manipulator of claim 6, wherein the tilting support cylinder
   includes a plurality of segments which rotatably support the rotating body inside thereof, as a result of being connected together in a circumferential direction.

9. The medical manipulator of claim 6, wherein teeth of the first bevel gear are enmeshed with teeth of a second bevel gear on a hollow cylindrical gear member, the pull wire inserted internally through a hollow portion of the hollow cylindrical gear member.

\* \* \* \* \*